(12) United States Patent
Ruijtenbeek et al.

(10) Patent No.: US 10,604,786 B2
(45) Date of Patent: Mar. 31, 2020

(54) METHOD FOR PREDICTING THE RESPONSE OF MELANOMA PATIENTS TO TARGETED PHARMACOTHERAPY

(71) Applicant: PAMGENE BV, 's-Hertogenbosch (NL)

(72) Inventors: Robby Ruijtenbeek, Utrecht (NL); Liesbeth Coosje Hovestad-Bijl, 's-Hertogenbosch (NL)

(73) Assignee: PAMGENE BV, 's-Hertogenbosch (NL)

(*) Notice: Subject to any disclaimer, the term of this patent is extended or adjusted under 35 U.S.C. 154(b) by 0 days.

(21) Appl. No.: 15/572,220

(22) PCT Filed: May 20, 2016

(86) PCT No.: PCT/EP2016/061361
§ 371 (c)(1),
(2) Date: Nov. 7, 2017

(87) PCT Pub. No.: WO2016/184999
PCT Pub. Date: Nov. 24, 2016

(65) Prior Publication Data
US 2018/0291423 A1  Oct. 11, 2018

(30) Foreign Application Priority Data
May 20, 2015 (EP) .................................... 15168371

(51) Int. Cl.
*C12Q 1/48* (2006.01)
*G01N 33/574* (2006.01)

(52) U.S. Cl.
CPC ......... *C12Q 1/485* (2013.01); *G01N 33/5743* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 8,962,267 B1 | 2/2015 | De Wijn et al. | |
| 2005/0187147 A1* | 8/2005 | Newman | A61K 31/337 514/1.7 |
| 2006/0234909 A1 | 10/2006 | Newman et al. | |
| 2007/0254295 A1 | 11/2007 | Harvey et al. | |
| 2010/0248265 A1 | 9/2010 | Hunter et al. | |
| 2011/0071052 A1* | 3/2011 | Hilhorst | C12Q 1/485 506/11 |
| 2011/0111980 A1 | 5/2011 | Houtman et al. | |
| 2011/0244465 A1 | 10/2011 | Harvey et al. | |
| 2012/0021939 A1 | 1/2012 | Ruijtenbeek et al. | |
| 2012/0035076 A1 | 2/2012 | Hilhorst et al. | |
| 2012/0115754 A1 | 5/2012 | Ruijtenbeek et al. | |
| 2013/0106812 A1 | 5/2013 | Miura | |
| 2013/0217055 A1 | 8/2013 | Boender et al. | |
| 2014/0287447 A1* | 9/2014 | Fiscus | C12Q 1/485 435/15 |
| 2014/0308678 A1 | 10/2014 | Hamamoto et al. | |

FOREIGN PATENT DOCUMENTS

| | | |
|---|---|---|
| EP | 2 239 571 A1 | 10/2010 |
| EP | 2 239 572 A1 | 10/2010 |
| EP | 2 239 579 A1 | 10/2010 |
| EP | 2 243 481 A1 | 10/2010 |
| WO | 2005035003 A2 | 4/2005 |
| WO | WO 2005/035003 A2 * | 4/2005 |
| WO | 2007109571 A2 | 9/2007 |
| WO | 2009125020 A1 | 10/2009 |
| WO | 2009130230 A2 | 10/2009 |
| WO | 2012049329 A1 | 4/2012 |
| WO | 2013080400 A1 | 6/2013 |
| WO | WO 2013/080400 A1 * | 6/2013 |
| WO | 2013106812 A1 | 7/2013 |
| WO | WO 2013/106812 A1 * | 7/2013 |

OTHER PUBLICATIONS

W Maat et al: Retrieved from the Internet: URL:https://www.pamgene.conn/upload/image/Applications notes/201009 (10-2010).pdf [retrieved on Nov. 19, 2015].*
Andliena Tahiri Etal: PLOS ONE.vol. 8, No. 8, Aug. 30, 2013 (Aug. 30, 2013), p. e72692.*
Bhullar et al (Molecular Cancer, 2018, 17:48, internet pp. 1-20).*
PCT International Search Report and Written Opinion dated Jun. 30, 2016 for PCT International Patent Application No. PCT/EP2016/061361, 20 pages.
Tahiri A et al: "Differential Inhibition of Ex-Vivo Tumor Kinase Activity by Vemurafenib in BRAF(V600E) and BRAF Wild-Type Metastatic Malignant Melanoma", PLOS ONE, vol. 8, No. 8, Aug. 30, 2013 (Aug. 30, 2013), p. e72692, XP055229685, 12 pages.
Maat, W et al: "Application Note—Protein Tyrosine Kinases; Target Discovery", Oct. 1, 2010 (Oct. 1, 2010), XP055229565, Retrieved from the Internet: URL:https://www.pamgene.com/upload/image/Applications notes/201009(10-2010).pdf.
Response to Written Opinion dated Mar. 16, 2017 in connection with PCT International Patent Application No. PCT/EP2016/061361, 4 pages.

* cited by examiner

*Primary Examiner* — Laura B Goddard
(74) *Attorney, Agent, or Firm* — Amster, Rothstein & Ebenstein LLP

(57) ABSTRACT

The present invention relates to a method for determining or predicting the response of a patient diagnosed with melanoma to targeted pharmacotherapy. The present invention also aims to provide methods and devices for predicting the response of patients diagnosed with melanoma to specific medicaments. More specifically, the present invention provides methods which measure kinase activity by studying phosphorylation levels and profiles and inhibitions thereof by drugs in samples of said patients.

11 Claims, 1 Drawing Sheet
Specification includes a Sequence Listing.

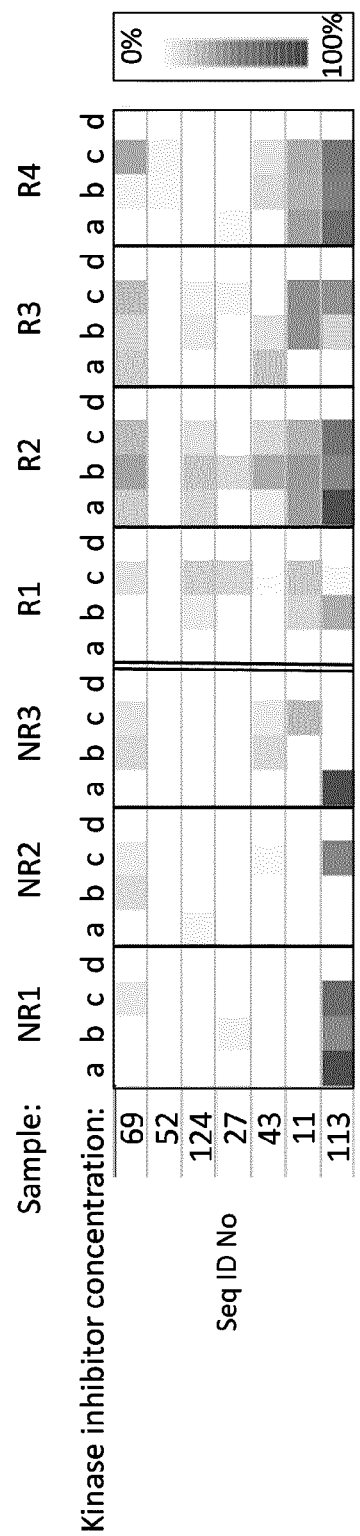

METHOD FOR PREDICTING THE RESPONSE OF MELANOMA PATIENTS TO TARGETED PHARMACOTHERAPY

CROSS-REFERENCE TO RELATED APPLICATIONS

This application is a U.S. national stage entry under 35 U.S.C. § 371 of PCT International Patent Application No. PCT/EP2016/061361, filed May 20, 2016, which claims priority to European Patent Application No. 15168371.1, filed May 20, 2015, the contents of which are incorporated herein by reference in their entirety.

FIELD OF THE INVENTION

The present invention relates to a method for determining or predicting the response of a patient diagnosed with melanoma to targeted pharmacotherapy. The present invention also aims to provide methods and devices for predicting the response of patients diagnosed with melanoma to specific medicaments. More specifically, the present invention provides methods which measure kinase activity by studying phosphorylation levels and profiles and inhibitions thereof by drugs in samples of said patients.

BACKGROUND OF THE INVENTION

Melanoma is a cancer that begins in the melanocytes. Melanocytes, the cells that can become melanoma, are also found in the epidermis. These skin cells make a brown pigment called melanin, which gives the skin its tan or brown colour. Melanin protects the deeper layers of the skin from some of the harmful effects of the sun. For most people, when skin is exposed to the sun, melanocytes make more of the pigment, causing the skin to tan or darken. Melanoma accounts for less than 2% of skin cancer cases but causes a large majority of skin cancer deaths. Melanoma is a cancer that begins in the melanocytes.

Melanoma remains a highly morbid disease and its incidence has continued to rise sharply over the past few decades. Overall incidence rates for melanoma are increasing among men and women. Since 1981, the rate of increase has been about 3% per year. According to estimates from the American Cancer Society, there were about 59,580 new cases of melanoma in the U.S. in 2005, and about 7,700 people died of this disease. Prior to 2009 the only FDA approved treatments for metastatic melanoma included dacarbazine, interferon-alpha, and interleukin-2. However, the prognosis of patients with disseminated disease remained poor, with a 5-year survival rate of 16% or less in the U.S. New treatments such as anti-angiogenic agents, Raf, Mek and other kinase inhibitors and vaccines are currently being developed and may offer improvements in survival for patients with this disease. In addition, the toll of melanoma in terms of "life-years lost" is the highest of all solid tumours in the United States.

For the diagnosis of melanoma a surface skin biopsy, punch biopsy or excisional biopsy is taken. Based on a primary biopsy diagnosis nearby lymph nodes may be biopsied to see if the cancer has spread. Staging of melanoma is based on the American Joint Committee on Cancer (AJCC) TNM system. The T stands for tumour (how far it has grown within the skin and other factors). The T category is assigned a number (from 0 to 4) based on the tumour's thickness (how far down it has grown). N stands for spread to nearby lymph nodes (bean-sized collections of immune system cells, to which cancers often spread first). The N category is assigned a number (from 0 to 3) based on whether the melanoma cells have spread to lymph nodes or are found in the lymphatic channels connecting the lymph nodes. The M category is based on whether the melanoma has metastasized (spread) to distant organs, which organs it has reached. According to these standards the different stages and survival in the US are as follows:

Stage IA: The 5-year survival rate is around 97%. The 10-year survival is around 95%.
Stage IB: The 5-year survival rate is around 92%. The 10-year survival is around 86%.
Stage IIA: The 5-year survival rate is around 81%. The 10-year survival is around 67%.
Stage IIB: The 5-year survival rate is around 70%. The 10-year survival is around 57%.
Stage IIC: The 5-year survival rate is around 53%. The 10-year survival is around 40%.
Stage IIIA: The 5-year survival rate is around 78%. The 10-year survival is around 68%.
Stage IIIB: The 5-year survival rate is around 59%. The 10-year survival is around 43%.
Stage IIIC: The 5-year survival rate is around 40%. The 10-year survival is around 24%.
Stage IV: The 5-year survival rate is about 15%-20%. The 10-year survival is about 10%-15%.

Melanoma treatment options are based on the stage of the disease and may include: surgery, chemotherapy, targeted therapy, immunotherapy and radiation therapy. Early-stage melanomas can often be treated effectively with surgery alone, but more advanced cancers often require other treatments.

Activating B-RAF V600E kinase mutations occur in 7% of human malignancies and 60% of melanomas. These changes cause the gene to make an altered BRAF protein that signals the melanoma cells to grow and divide quickly. A number of kinase inhibitors addressing BRAF and other kinase targets in the pathway including MEK have been approved for clinical use. These compounds include Vemurafenib (PLX4032 or RO5185426), Dabrafenib (GSK2118436) and Trametinib (GSK1120212). Several other kinase inhibitors are currently in clinical development for melanoma including AB1010 (Masitinib), AEB071 (Sotrastaurin), AG013736 (Axitinib), AMN107 (nilotinib), ARQ 197 (Tivantinib), ARRY-438162 (Binimetinib), AS703026 MSC1936369B (Pimasertib), AZD2644 (Selumetinib), BAY 43-9006 (Sorafenib), BEZ235 (Dactolisib), BKM120 (Buparlisib), BMS-908662, CEP-32496, E7050 (Golvatinib), E7080 (Lenvatinib), GDC-0973 (Cometinib), LEE011 (Ribociclib), LGX818 (Encorafenib), LY2801653, LY3009120, MLN2480, P276-00 (Riviciclib), PD-0325901, PLX3397, PLX3603, Vemurafenib, PLX7486, PLX8394, PX-866 (Sonolisib), RAF265, RO4987655, SAR260301, TAK-733, TK1258 (Dovitinib), XL184 (Cabozantinib) and XL281.

While early-stage melanomas can often be cured with surgery, more advanced melanomas can be much harder to treat because standard cancer treatments such as chemotherapy are not very effective. But in recent years, newer types of immunotherapy and targeted therapies have changed the treatment of this disease, and many new treatments have shown a great deal of promise in treating advanced melanomas.

In particular, stage IV melanomas are very hard to cure, as they have already spread to distant lymph nodes or other areas of the body. While the skin tumours can often be removed by surgery or treated with radiation therapy, metastases in internal organs which cannot be removed may be treated with radiation, immunotherapy, targeted therapy, or chemotherapy. In about half of all melanomas with mutations in the BRAF gene, treatment with targeted drugs such as vemurafenib, dabrafenib and trametinib are used. These drugs can help some people live longer, although they have not been shown to cure these melanomas. Even though the outlook for patients with stage IV melanoma tends to be poor overall, a small number of patients respond very well to treatment and survive for many years after diagnosis.

Unfortunately, also most anti-tumour treatments are associated with undesirable side effects, such as profound nausea, vomiting, or severe fatigue. Also, while anti-tumour treatments have been successful, they do not produce significant clinical responses in all patients who receive them resulting in undesirable side effects, delays, and costs associated with ineffective treatment. Therefore, biomarkers that can be used to predict the response of a subject to an antitumor agent prior to administration thereof are greatly needed.

Given the high incidence of melanoma and limited efficacy of current treatments, a melanoma biomarker and assay for a melanoma biomarker is needed that could serve as an accurate early indicator for therapeutic response in a mammalian subject to measure the effectiveness of candidate melanoma inhibitory agents.

In view of the above, there remains a pressing need for methods that provide a fast and accurate prediction of the response of a patient diagnosed with melanoma to targeted pharmacotherapy. These methods would enable to provide information regarding the efficacy of the targeted pharmacotherapy treatment, and more specifically provide an early determination of the most suited treatment of the melanoma patient.

The present invention aims at providing methods and devices for predicting the response of a patient diagnosed with melanoma to targeted pharmacotherapy. The present invention also aims to provide methods and devices for predicting the response of patients diagnosed with melanoma to specific medicaments. The method of the present invention therefore adds to the existing assays currently used to select therapies in melanoma patients.

SUMMARY OF THE INVENTION

The present invention provides methods and devices that enable the determination of the response of a patient diagnosed with melanoma to targeted pharmacotherapy by measuring kinase activity of a melanoma sample (or sample of a metastasis thereof) in the presence and absence of a kinase inhibitor.

In a first aspect the present invention provides in a method for predicting the response of a patient diagnosed with melanoma cancer, to a medicament, comprising the steps of:
(a) measuring the kinase activity of a sample, obtained from the melanoma tumour or a metastasis thereof from said patient, by contacting said sample with a set of protein kinase substrate comprising at least the peptide markers with SEQ ID NO 11, 27, 43, 52, 69, 113 and 124 in the presence and in the absence of a kinase inhibitor, thereby providing a phosphorylation profile of said sample in the presence of said kinase inhibitor and a phosphorylation profile of said sample in the absence of said kinase inhibitor; and,
(b) determining from said phosphorylation profiles in the presence and in the absence of said kinase inhibitor the differential phosphorylation level, said differential phosphorylation level predicting the response of said patient to said medicament.

The method according to the invention provides that said phosphorylation profiles comprise the phosphorylation levels of phosphorylation sites present in at least 30 of the peptide markers as listed in Table 1. Particularly, the method according to the invention provides that said phosphorylation profiles comprise the phosphorylation levels of phosphorylation sites present in the peptide markers as listed in Table 1.

The method according to the invention further provides that step (b) is replaced by step (c) comparing said phosphorylation profile of said sample in the presence of said kinase inhibitor with said phosphorylation profile of said sample in the absence of said kinase inhibitor, thereby determining a classifier parameter; and a step (d) predicting the response of said patient to said medicament on the basis of said classifier parameter. In particular, said classifier parameter predicts the response of said patient to said medicament if said classifier parameter is above a first predetermined threshold level, and wherein said classifier parameter indicates non-response to said medicament of said patient if said classifier parameter is below a second predetermined threshold level.

The method according to the invention further provides that said medicament is chosen from the list comprising Vemurafenib, Dabrafenib, Trametinib, AB1010 (Masitinib), AEB071 (Sotrastaurin), AG013736 (Axitinib), AMN107 (nilotinib), ARQ 197 (Tivantinib), ARRY-438162 (Binimetinib), AS703026 MSC1936369B (Pimasertib), AZD2644 (Selumetinib), BAY 43-9006 (Sorafenib), BEZ235 (Dactolisib), BKM120 (Buparlisib), BMS-908662, CEP-32496, E7050 (Golvatinib), E7080 (Lenvatinib), GDC-0973 (Cometinib), LEE011 (Ribociclib), LGX818 (Encorafenib), LY2801653, LY3009120, MLN2480, P276-00 (Riviciclib), PD-0325901, PLX3397, PLX3603, Vemurafenib, PLX7486, PLX8394, PX-866 (Sonolisib), RAF265, RO4987655, SAR260301, TAK-733, TK1258 (Dovitinib), XL184 (Cabozantinib) and/or XL281, and wherein said kinase inhibitor is chosen from the list comprising Vemurafenib, Dabrafenib, Trametinib, AB1010 (Masitinib), AEB071 (Sotrastaurin), AG013736 (Axitinib), AMN107 (nilotinib), ARQ 197 (Tivantinib), ARRY-438162 (Binimetinib), AS703026 MSC1936369B (Pimasertib), AZD2644 (Selumetinib), BAY 43-9006 (Sorafenib), BEZ235 (Dactolisib), BKM120 (Buparlisib), BMS-908662, CEP-32496, E7050 (Golvatinib), E7080 (Lenvatinib), GDC-0973 (Cometinib), LEE011 (Ribociclib), LGX818 (Encorafenib), LY2801653, LY3009120, MLN2480, P276-00 (Riviciclib), PD-0325901, PLX3397, PLX3603, Vemurafenib, PLX7486, PLX8394, PX-866 (Sonolisib), RAF265, RO4987655, SAR260301, TAK-733, TK1258 (Dovitinib), XL184 (Cabozantinib), XL281 and/or analogs thereof. More in particular, the method is provided with the proviso that said medicament and said kinase inhibitor are different compounds, and preferably wherein said medicament is Vemurafenib and said kinase inhibitor is Dabrafenib.

The method according to the invention further provides that said differential phosphorylation level or said classifier parameter predicts a response, non-response or undetermined or intermediate prediction of the effect of said medicament on said patient.

The method according to the invention further provides that said phosphorylation sites are present on proteins, peptides or peptide mimetics immobilized on a solid support, and preferably a porous solid support.

The method according to the invention further provides that said peptide markers are serine and/or threonine containing peptides.

The method according to the invention further comprises repeating the method steps for different concentrations of the kinase inhibitor, thereby generating phosphorylation profiles and differential phosphorylation levels in function of the kinase inhibitor concentration.

The method according to the invention further provides that said melanoma is a BRAF V600 mutation positive melanoma.

In a second aspect the present invention provides in a computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out the method according to the invention.

In a third aspect the present invention provides in a kit for determining the response of a patient diagnosed with melanoma, to a medicament, comprising at least one array comprising peptide markers with SEQ ID NO 11, 27, 43, 52, 69, 113 and 124, and a computer readable storage medium having recorded thereon one or more programs for carrying out the method according to the invention.

In a fourth aspect the present invention provides in the use of peptide markers with SEQ ID NO 11, 27, 43, 52, 69, 113 and 124 for predicting the response of a patient diagnosed with melanoma cancer to a medicament.

BRIEF DESCRIPTION OF FIGURES

FIG. 1 shows that the method according to the invention using Dabrafenib as kinase inhibitor allows a good prediction of the treatment outcome of patients treated with Vemurafenib.

DETAILED DESCRIPTION OF THE INVENTION

Before the present method and devices used in the invention are described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

In this specification and the appended claims, the singular forms "a", "an", and "the" include plural references unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The present invention provides methods and devices that enable the determination of the response of a patient diagnosed with melanoma to targeted pharmacotherapy by measuring kinase activity of a melanoma sample (or sample of a metastasis thereof) in the presence and absence of a kinase inhibitor. The present invention further shows how the method and devices can be used to predict the response of patients diagnosed with melanoma to that specific kinase inhibitor or to other medicaments. The method of the present invention therefore adds to the existing assays currently used to select therapies in melanoma patients. In one embodiment of the present invention, methods are provided wherein the kinase activity is protein kinase activity. For purposes of the present invention, and as used herein the term "enzyme activity", "kinase activity" or "protein kinase activity" refer to the formation of reaction product(s) by a certain amount of enzyme, kinase or protein kinase acting on a substrate during the course of the assay.

Protein kinase activity is referred to as the activity of protein kinases. A protein kinase is a generic name for all enzymes that transfer a phosphate to a protein. About three to four percent of the human genome contains transcription information for the formation of protein kinases. Currently, there are about 518 known different protein kinases. However, because three to four percent of the human genome is a code for the formation of protein kinases, there may be many more separate kinases in the human body.

A protein kinase is a kinase enzyme that modifies other proteins by covalently coupling phosphate groups to them. This process or activity is also referred to as phosphorylation. Phosphorylation can therefore be regarded as the process of the addition of a phosphate group to a substrate. Phosphorylation usually results in a functional change of the substrate by changing enzyme activity, cellular location, or association with other proteins. Up to 30% of all proteins may be modified by kinase activity, and kinases are known to regulate the majority of cellular pathways, especially those involved in signal transduction, the transmission of signals within the cell. The chemical activity of a kinase involves removing a phosphate group from ATP or GTP and covalently attaching it to amino acids such as serine, threonine, tyrosine, histidine, aspartic acid and/or glutamic acid that have a free hydroxyl group. Most known kinases act on both serine and threonine, others act on tyrosine, and a number act on all serine, threonine and tyrosine. The protein kinase activity monitored with the method of the present invention is preferably directed to protein kinases acting towards serine, threonine and/or tyrosine, preferably acting on both serine and threonine, on tyrosine or on serine, threonine and tyrosine and more preferably the method of the present invention if preferably directed to protein kinases acting towards serine and threonine.

Protein kinases are distinguished by their ability to phosphorylate substrates on discrete sequences. These sequences have been determined by sequencing the amino acids around the phosphorylation sites and are usually distinct for each protein kinase. The recognition sequence on each substrate is specific for each kinase catalyst.

Because protein kinases have profound effects on a cell, their activity is highly regulated. Kinases are turned on or off by for instance phosphorylation, by binding of activator proteins or inhibitor proteins, or small molecules, or by controlling their location in the cell relative to their substrates. Deregulated kinase activity is a frequent cause of disease, particularly cancer, where kinases regulate many aspects that control cell growth, movement and death. Therefore monitoring the protein kinase activity in tissues can be of great importance and a large amount of information can be obtained when comparing the kinase activity of different tissue samples.

As described in the present invention, the inventors have surprisingly found that the response of a patient diagnosed with melanoma to targeted pharmacotherapy can be predicted and/or determined on the basis of the measurement of the kinase activity of a sample taken from the melanoma or a metastasis thereof.

The measurement of the kinase activity is performed by contacting a melanoma sample with one or more substrates, preferably protein kinase substrates, thereby generating a phosphorylation profile.

Said protein kinase substrates as used herein, are preferably peptides, proteins or peptide mimetics. The protein kinase substrates each comprise, preferably one or more, phosphorylation sites that can be phosphorylated by the protein kinases present in the sample. Therefore, exposure of a protein kinase substrate to a sample comprising a protein kinase results in the phosphorylation of one or more of the phosphorylation sites of the protein kinase substrate. This phosphorylation activity can be measured using techniques known in the art. Therefore, during the measurement method the kinase enzymes present in the sample will phosphorylate, preferably one or more, of the phosphorylation sites on one or more protein kinase substrates. The inventors have observed essential differences between kinase activity of melanoma tumours having a different response to targeted pharmacotherapy. Consequently, the inventors have observed that the kinases present in a melanoma sample will phosphorylate protein kinase substrates differently depending on the response to targeted pharmacotherapy. Phosphorylation signals differ between the samples, resulting in phosphorylation patterns that differ depending on response to targeted pharmacotherapy. The effect has been observed to be even more significant when phosphorylation profiles and/or levels in the absence of a protein kinase inhibitor are compared to measurements in the presence of a protein kinase inhibitor.

For purposes of the present invention, and as used herein the term "pharmacotherapy", or "pharmacotherapeutics" or "drug treatment" refers to the use of a pharmaceutical drug, also referred to as medicine or medicament wherein said pharmacotherapy is intended for use in the diagnosis, cure, mitigation, treatment, or prevention of disease.

The present invention therefore provides in a method for predicting the response of a patient diagnosed with melanoma cancer, to a medicament, comprising the steps of:
(a) measuring the kinase activity of a sample, obtained from the melanoma tumour from said patient, by contacting said sample with a set of protein kinase substrate comprising at least the peptide markers with SEQ ID NO 11, 27, 43, 52, 69, 113 and 124 in the presence and in the absence of a kinase inhibitor, thereby providing a phosphorylation profile of said sample in the presence of said kinase inhibitor and a phosphorylation profile of said sample in the absence of said kinase inhibitor; and,
(b) determining from said phosphorylation profiles in the presence and in the absence of said kinase inhibitor the differential phosphorylation level, said differential phosphorylation level predicting the response of said patient to said medicament.

It is clear that effects of a medicament can be monitored using this method. The medicament and/or the kinase inhibitor affects the degree of inhibition, the potency and/or the selectivity of the kinases in the sample. More peptide inhibition is caused by the larger effect of the medicament on the kinases in the sample and therefore the drug is less selective. Also an increased peptide inhibition would lead to a larger amount of normal tissues being affected by the drug, making the drug less tumour tissue specific.

As referred to in the present application melanoma regards a specific type of skin cancer which forms from melanocytes (pigment-containing cells in the skin). While other types of skin cancer (e.g. basal cell cancer (BCC) and squamous cell cancer (SCC)) are more common, melanoma is considered to be much more dangerous if it is not found in the early stages. It causes the majority (75%) of deaths related to skin cancer. Globally, in 2012, melanoma occurred in 232,000 people and resulted in 55,000 deaths. About 60% of melanomas contain a mutation in the B-Raf gene. Early clinical trials suggested that B-Raf inhibitors including Vemurafenib could lead to substantial tumour regression in a majority of patients if the tumour contains the B-Raf mutation. However, there still remains room for improvement.

As used in the present invention, the term "sample" refers to a sample obtained from an organism (patient) such as human or from components (e.g. tissue or cells) of such an organism. Said sample is preferably obtained from a patient diagnosed with melanoma and needs to be derived from the tumour tissue of said patient. Accordingly the sample may be taken from the melanoma tissue or a metastasis thereof. More preferably said melanoma sample (or the metastasis sample) is a surface skin biopsy, punch biopsy, excisional biopsy, tumour tissue biopsy, vacuum assisted biopsy, fine needle biopsy or material from a resected tumour. Said sample is thereby referred to as a 'clinical sample' which is a sample derived from a melanoma patient.

Said tumour tissue sample is preferably a fresh or a fresh frozen sample.

More preferably, said sample refers to a lysate of a melanoma tumour tissue obtained through surface skin biopsy, punch biopsy, excisional biopsy, tumour tissue biopsy, fine needle biopsy or material from a resected tumour.

Alternatively said sample may be derived from a melanoma tumour sample tissue or a metastasis thereof that has been cultured in vitro for a limited period of time. Said sample may be obtained from specific melanoma cell lines and in particular cell lysates thereof.

In a preferred embodiment of the present invention said sample is a sample that has undergone a preparation step prior to the steps according to the method of the present invention. Preferably said preparation step is a step where the protein kinases present in said sample are released from the tissue by lysis. Additionally the kinases in the sample may be stabilized, maintained, enriched or isolated, and the measurement of the kinase activity as performed in step (a) occurs on the enriched or isolated protein kinase sample. By first enriching protein kinases in the sample or isolating protein kinases from the sample the subsequent measurement of the kinase activity will occur in a more efficient and reliable manner. Also the clarity and intensity of the obtained phosphorylation signal will be increased as certain contaminants are being removed during the enriching or isolating step.

As used in the present invention, the term "phosphorylation profile" refers to a data set representative for the phosphorylation levels of, preferably one or more, phosphorylation sites present on the protein kinase substrates. When measuring the kinase activity of a sample by contacting said sample with protein kinase substrates a specific phosphorylation profile is obtained. The phosphorylation profile is generated by the phosphorylation of the protein kinase substrates with the protein kinases present in the sample and it comprises the level of phosphorylation of the phosphorylation sites present on the protein kinase substrates used. A phosphorylation profile can thus be generated when using at least one protein kinase substrate in different test conditions such as for example by comparing the phosphorylation of a sample on one peptide or protein (protein kinase substrate) in the presence and absence of a protein kinase inhibitor. More frequently phosphorylation profiles of a sample will be measured using several protein kinase substrates in the same or sequentially carried out experiments. Preferably, the present invention determines serine and threonine kinase activity levels or profiles.

It should be noted that a person skilled in the art will appreciate that the methods of the present invention can use phosphorylation profiles as a basis for determining the predicting the response to a medicament of a patient suffering from melanoma. However, the phosphorylation levels of individual protein kinase substrates can also be used as a basis for determining or predicting the response to a medicament of a patient suffering from melanoma.

It should be noted that for the measurement of the protein kinase activity, ATP or any other phosphate source needs to be added to the sample when it is contacted with the protein kinase substrates. The presence of ATP will lead to a phosphorylation of the protein kinase substrates. Alternatively, the phosphorylation of the protein kinase substrates can be performed in the absence of exogenous ATP. When no ATP is added during the incubation of the sample with the protein kinase substrates, the endogenous ATP, the ATP naturally present in the sample, will act as the primary source of ATP.

The phosphorylation level of each of the protein kinase substrates can be monitored using any method known in the art. The response of the protein kinase substrates is determined using a detectable signal, said signal resulting from the interaction of the sample with the protein kinase substrates or by for instance measuring mass differences using mass spectrometry. In determining the interaction of the sample with the protein kinase substrates the signal is the result of the interaction of the phosphorylated substrates with a molecule capable of binding to the phosphorylated substrates. This binding can be detected by e.g. surface plasmon resonance or by the molecule being detectably labelled. For the latter, the molecule that specifically binds to the substrates of interest (e.g. antibody or polynucleotide probe) can be detectably labelled by virtue of containing an atom (e.g. radionuclide), molecule (e.g. fluorescein), or enzyme or particle or complex that, due to a physical or chemical property, indicates the presence of the molecule. A molecule may also be detectably labelled when it is covalently bound to or otherwise associated with a "reporter" molecule (e.g. a biomolecule such as an enzyme) that acts on a substrate to produce a detectable atom, molecule or other complex.

Detectable labels suitable for use in the present invention include any composition detectable by spectroscopic, photochemical, biochemical, immunochemical, electrical, optical or chemical means. Labels useful in the present invention include biotin for staining with labelled avidin or streptavidin conjugate, magnetic beads (e.g. Dynabeads'), fluorescent dyes (e.g. fluorescein, fluorescein-isothiocyanate (FITC), Texas red, rhodamine, green fluorescent protein, enhanced green fluorescent protein and related proteins with other fluorescence emission wavelengths, lissamine, phycoerythrin, Cy2, Cy3, Cy3.5, Cy5, Cy5.5, Cy7, FluorX [Amersham], SYBR Green I & II [Molecular Probes], and the like), radiolabels (e.g. 3H, 125I, 35S, 14C, or 32P), enzymes (e.g. hydrolases, particularly phosphatases such as alkaline phosphatase, esterases and glycosidases, or oxidoreductases, particularly peroxidases such as horse radish peroxidase, and the like), substrates, cofactors, chemiluminescent groups, chromogenic agents, and colorimetric labels such as colloidal gold or coloured glass or plastic (e. g. polystyrene, polypropylene, latex, etc.), protein particles or beads.

Means of detecting such labels are well known to those of skill in the art. Thus, for example, chemiluminescent and radioactive labels may be detected using photographic film or scintillation counters, and fluorescent markers may be detected using a photodetector to detect emitted light (e.g. as in fluorescence-activated cell sorting). Enzymatic labels are typically detected by providing the enzyme with a substrate and detecting a coloured reaction product produced by the action of the enzyme on the substrate. Colorimetric labels are detected by simply visualizing the coloured label. Thus, for example, where the label is a radioactive label, means for detection include a scintillation counter, photographic film as in autoradiography, or storage phosphor imaging. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Also, simple colorimetric labels may be detected by observing the colour associated with the label. Fluorescence resonance energy transfer has been adapted to detect binding of unlabeled ligands, which may be useful on arrays.

In a particular embodiment of the present invention the response of the protein kinase substrates to the sample is determined using detectably labelled antibodies; more in particular fluorescently labelled antibodies. In those embodiments of the invention where the substrates consist of protein kinase substrates, the response of the protein kinase substrates is determined using fluorescently labelled anti-phosphotyrosine antibodies, fluorescently labelled anti-phosphoserine or fluorescently labelled anti-phosphothreonine antibodies. The use of fluorescently labelled anti-phosphotyrosine antibodies or fluorescently labelled anti-phosphoserine or fluorescently labelled anti-phosphothreonine antibodies in the method of the present invention, allows real-time or semi real-time determination of the protein kinase activity and accordingly provides the possibility to express the protein kinase activity as the initial velocity of protein kinase derived from the activity over a certain period of incubation of the sample on the protein kinase substrates.

The inventors have found that measuring the kinase activity of the sample in the presence and in the absence of a protein kinase inhibitor, enables an even better differentiation between the prediction of the response of a targeted pharmacotherapy of melanoma patients. This surprising effect is due to the differences in protein kinase activity between different individual patients and their respective tumours. The difference can be reduced by comparing the protein kinase activity profiles in the presence and absence of a protein kinase inhibitor between different patients. This enables a more accurate classification of the prediction of the response of a targeted pharmacotherapy.

The term "differential phosphorylation level" as used herein therefore refers to a data set comprising comparison data from the phosphorylation profiles in the presence and in the absence of a protein kinase inhibitor. The statistical analysis of the differential phosphorylation level can be done using multivariate and/or univariate statistical methods known in the art.

The differential phosphorylation levels are obtained by (numerically) comparing the peptide phosphorylation levels or profiles in the presence and in the absence of the protein kinase inhibitor in the same sample, for instance, but not limited to, providing ratios or differences of the profiles obtained in the presence and the absence of the protein kinase inhibitor.

In addition, because the differential phosphorylation level is generated by comparing the phosphorylation levels or profiles of the same sample in the presence and the absence of the protein kinase inhibitor, preferably during a parallel series of measurements run in the same instrument, the differential phosphorylation level is surprisingly found to be less affected by variation, for example biological variation, experimental variation, compared to single phosphorylation levels or profiles. This provides a more robust, more sensitive, more reproducible and more reliable method for determining the prediction of pharmacotherapy response in melanoma patients.

Moreover, the measurement of the kinase activity of said sample preferably occurs by contacting said sample with at least the peptide markers with SEQ ID NO 11, 27, 43, 52, 69, 113 and 124 in the presence and in the absence of a protein kinase inhibitor. Techniques from the prior art often require the incubation of the cells or tissues with said compounds preferably in vivo, during the culturing of the cells or tissues or during a large time period prior to the actual measurement of the kinase activity. The present invention provides that the protein kinase inhibitor is added directly to the sample and preferably directly to the lysate sample. The protein kinase inhibitor(s) is added to the sample only just prior to contacting the sample with the protein kinase substrates and performing the kinase activity assay. Consequently, the protein kinase inhibitor(s) is added in vitro at the time the incubation of the lysate sample with the protein kinase substrates is initiated. The present invention therefore provides an in vitro screening tool which allows the use of a single sample which is split into a first part that is used for the incubation of the sample in the absence of a protein kinase inhibitor while a second part of the sample is used for the incubation of the sample in the presence of a protein kinase inhibitor(s).

In another embodiment according to the present invention, the phosphorylation profiles comprise the phosphorylation levels of phosphorylation sites present in at least 30 of the peptide markers as listed in Table 1. Preferably phosphorylation levels will be studied of phosphorylation sites present in at least 7, 8, 9 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141 or 142 of the peptide markers listed in Table 1, comprising at least peptide markers with SEQ ID NO 11, 27, 43, 52, 69, 113 and 124.

In another embodiment according to the present invention, the phosphorylation profiles comprise the phosphorylation levels of phosphorylation sites present in the peptide markers as listed in Table 1.

The term "peptide markers" in the context of the present invention refers to the fact that the peptides as listed in Table 1 can be preferably used according to the methods of the present invention to measure the phosphorylation levels of phosphorylation sites of said markers in the presence of protein kinase present in samples. The phosphorylation levels of the individual phosphorylation sites present in said markers may be measured and compared in different ways. Therefore the present invention is not limited to the use of peptides identical to any of these peptide markers as listed in Table 1 as such. The skilled person may easily on the basis of the peptide markers listed in Table 1 design variant peptides compared to the specific peptides in said Table and use such variant peptides in a method for measuring phosphorylation levels of phosphorylation sites common to said peptide markers as listed in Table 1. These variant peptides may have one or more (2, 3, 4, 5, 6, 7, etc.) amino acids more or less than the given peptides and may also have amino acid substitutions (preferably conservative amino acid substitutions) as long as these variant peptides retain at least one or more of the phosphorylation sites of said original peptides as listed in said table. Further the skilled person may also easily carry out the methods according to the present invention by using proteins (full length or N- or C-terminally truncated) comprising the amino acid regions of the "peptide markers" listed in Table 1 as sources for studying the phosphorylation of sites present in the amino acid regions of the peptides listed in Table 1. Also the skilled person may use peptide mimetics.

The protein kinase substrates as used in the methods described herein, are meant to include peptides, proteins or peptide mimetics comprising, preferably one or more, of the phosphorylation sites of the peptide markers of Table 1. Said one or more phosphorylation sites are specifically phosphorylated by the protein kinases present in the sample thereby providing a phosphorylation profile. More preferably the protein kinase substrates (peptides, proteins or peptide mimetics) as used in the method of the present invention comprise at least the peptide markers with SEQ ID NO 11, 27, 43, 52, 69, 113 and 124 as listed in Table 1. More particularly said protein kinase substrates represent the one or more phosphorylation sites present in at least 7, 8, 9 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141 or 142 of the peptide markers listed in Table 1, at least comprising peptide markers with SEQ ID NO 11, 27, 43, 52, 69, 113 and 124. In a more preferred embodiment the protein kinase substrates comprise or consist of, preferably one or more, phosphorylation sites present in all of the peptide markers listed in Table 1.

The inventors have found that especially the peptide markers with SEQ ID NO 11, 27, 43, 52, 69, 113 and 124 as listed in Table 1 enable the prediction of pharmacotherapy response in melanoma patients.

TABLE 1 list of 142 peptide markers comprising phosphorylation sites used for determining the kinase activity, their sequence and SEQ ID NO The name of the peptide markers refers to the associated proteins and also refers to the start and the end position of the amino acid sequence.

| SEQ ID NO | Name | Sequence |
|---|---|---|
| 1 | ANDR_785_797_S791 | VRMRHLSQEFGWL |
| 2 | ATM_1972_1984_S1974/S1981/S1983/T1984 | KRSLAFEEGSQST |
| 3 | BAD_112_124_S118/S124 | RELRRMSDEFVDS |
| 4 | BAD_69_81_S71/S74/S75/T80 | IRSRHSSYPAGTE |
| 5 | BAD_93_105_S97/S99 | FRGRSRSAPPNLW |
| 6 | BRCA1_1451_1463_S1457/S1460/S1461/T1456 | EKAVLTSQKSSEY |
| 7 | C1R_201_213_S202/S206/S207/S213 | ASGYISSLEYPRS |
| 8 | CDN1A_139_151_S146/T145/T148 | GRKRRQTSMTDFY |
| 9 | CDN1B_151_163_S160/S161/T157/T162 | IRKRPATDDSSTQ |
| 10 | E1A_ADE05_212_224_S219/S222/T218 | AILRRPTSPVSRE |
| 11 | FRAP_2443_2455_S2448/S2450/S2454/T2444/T2446 | RTRTDSYSAGQSV |
| 12 | FRAP_2475_2487_S2478/S2481 | VPESIHSFIGDGL |
| 13 | IF4E_203_215_S207/S209/T203/T205/T210/T211 | TATKSGSTTKNRF |
| 14 | IKBA_26_38_S32/S36 | LDDRHDSGLDSMK |
| 15 | IKKB_173_185_C179A_S177/S181/T180/T185 | LDQGSLATSFVGT |
| 16 | IKKB_686_698_S689/S692/S695/S697/T693 | QLMSQPSTASNSL |
| 17 | KS6A1_374_386_S380/T384 | QLFRGFSFVATGL |
| 18 | LIPS_944_956_S950/S951/T955 | GFHPRRSSQGATQ |
| 19 | MPIP1_172_184_S178/T173 | FTQRQNSAPARML |
| 20 | NOS3_1171_1183_S1171/S1177/S1179/T1175 | SRIRTQSFSLQER |
| 21 | P53_12_24_S15/S20/T18 | PPLSQETFSDLWK |

TABLE 1-continued list of 142 peptide markers comprising phosphorylation sites used for determining the kinase activity, their sequence and SEQ ID NO The name of the peptide markers refers to the associated proteins and also refers to the start and the end position of the amino acid sequence.

| SEQ ID NO | Name | Sequence |
|---|---|---|
| 22 | PDPK1_27_39_S27/S35/S36/T31/T33/T37 | SMVRTQTESSTPP |
| 23 | PRKDC_2618_2630_S2624/S2626/T2618/T2620 | TRTQEGSLSARWP |
| 24 | RAF1_253_265_S257/S259/T258/T260 | QRQRSTSTPNVHM |
| 25 | RB_350_362_S350/S360/T353/T356 | SFETQRTPRKSNL |
| 26 | RB_774_786_S780/T774/T778 | TRPPTLSPIPHIP |
| 27 | RB_803_815_S807/S811 | NIYISPLKSPYKI |
| 28 | TOP2A_1463_1475_S1469/S1471/S1474/T1470 | RRKRKPSTSDDSD |
| 29 | TY3H_65_77_S71 | FIGRRQSLIEDAR |
| 30 | YAP1_121_133_S127/S128/S131 | QHVRAHSSPASLQ |
| 31 | ACM1_421_433_T428 | CNKAFRDTFRLLL |
| 32 | ACM1_444_456_S451/T455 | KIPKRPGSVHRTP |
| 33 | ACM4_456_468_T459/T463 | CNATFKKTFRHLL |
| 34 | ACM5_494_506_T501/T505 | CYALCNRTFRKTF |
| 35 | ACM5_498_510_T501/T505 | CNRTFRKTFKMLL |
| 36 | ADDB_696_708_S697/S699/S701/S703 | GSPSKSPSKKKKK |
| 37 | ADDB_706_718_S713/S718/T711 | KKKFRTPSFLKKS |
| 38 | ADRB2_338_350_S345/S346 | ELLCLRRSSLKAY |
| 39 | AKT1_301_313_T305/T308/T312 | KDGATMKTFCGTP |
| 40 | ANXA1_209_221_T216 | AGERRKGTDVNVF |
| 41 | ART_025_CXGLRRWSLGGLRRWSL_SNA/TNA | GLRRWSLGGLRRWSL |
| 42 | ATF2_47_59_T51/T53/T55 | VADQTPTPTRFLK |
| 43 | BCKD_45_57_S47/S52/S57/T49/T51 | ERSKTVTSFYNQS |
| 44 | CA2D1_494_506_T501/T505 | LEDIKRLTPRFTL |
| 45 | CAC1C_1974_1986_S1975/S1981 | ASLGRRASFHLEC |
| 46 | CD27_212_224_S219/S224 | HQRRKYRSNKGES |
| 47 | CDC2_154_169_T161/T166 | GIPIRVYTHEVVTLWY |
| 48 | CDK7_163_175_S164/T170/T175 | GSPNRAYTHQVVT |
| 49 | CENPA_1_14_S7 | MGPRRRSRKPEAPR |
| 50 | CFTR_730_742_S737/S742 | EPLERRLSLVPDS |
| 51 | CFTR_761_773_S768 | LQARRRQSVLNLM |

TABLE 1-continued list of 142 peptide markers comprising phosphorylation sites used for determining the kinase activity, their sequence and SEQ ID NO. The name of the peptide markers refers to the associated proteins and also refers to the start and the end position of the amino acid sequence.

| SEQ ID NO | Name | Sequence |
|---|---|---|
| 52 | CGHB_109_121_S116/T117/T118 | QCALCRRSTTDCG |
| 53 | COF1_17_29_S23/S24/T25 | DMKVRKSSTPEEV |
| 54 | CREB1_126_138_S129/S133 | EILSRRPSYRKIL |
| 55 | CSF1R_701_713_S713 | NIHLEKKYVRRDS |
| 56 | CSK21_355_367_S356/S357/S362/T360 | ISSVPTPSPLGPL |
| 57 | DCX_49_61_S57/T56 | HFDERDKTSRNMR |
| 58 | DESP_2842_2854_S2843/S2845/S2849/T2853 | RSGSRRGSFDATG |
| 59 | ELK1_356_368_T359/T361/T363/T368 | LLPTHTLTPVLLT |
| 60 | ELK1_410_422_S411/S416/S422/T417 | ISVDGLSTPVVLS |
| 61 | EPB42_241_253_S248 | LLNKRRGSVPILR |
| 62 | ERBB2_679_691_T686 | QQKIRKYTMRRLL |
| 63 | ERF_519_531_S531/T526 | GEAGGPLTPRRVS |
| 64 | ESR1_160_172_S167/T168 | GGRERLASTNDKG |
| 65 | F263_454_466_S461/T463 | NPLMRRNSVTPLA |
| 66 | FIBA_569_581_S572/S576/S577/S578/S580 | EFPSRGKSSSYSK |
| 67 | FOXO3_25_37_S26/S30/T32 | QSRPRSCTWPLQR |
| 68 | GBRB2_427_439_S427/S434/T439 | SRLRRRASQLKIT |
| 69 | GPR6_349_361_S350/S356/S358/S360 | QSKVPFRSRSPSE |
| 70 | GPSM2_394_406_S401 | PKLGRRHSMENME |
| 71 | GRIK2_708_720_S710/S711/S715/S720 | FMSSRRQSVLVKS |
| 72 | GSUB_61_73_T68 | KKPRRKDTPALHI |
| 73 | GYS2_1_13_S6/S8/S11/T10 | MLRGRSLSVTSLG |
| 74 | H2B1B_27_40_S33/S37/S39 | GKKRKRSRKESYSI |
| 75 | H32_3_18_S11/T4/T7/T12 | RTKQTARKSTGGKAPR |
| 76 | K6PL_766_778_S775/T770/T773 | LEHVTRRTLSMDK |
| 77 | KAP2_92_104_S92/S99/T104 | SRFNRRVSVCAET |
| 78 | KAP3_107_119_S114/T110 | NRFTRRASVCAEA |
| 79 | KAPCG_192_206_T196/T198/T202 | VKGRTWTLCGTPEYL |
| 80 | KCC2G_278_289_S280/T287 | VASMMHRQETVE |
| 81 | KCNA1_438_450_S439/S442/S445/S446/S447/S450/T448 | DSDLSRRSSSTMS |
| 82 | KCNA2_442_454_S447/S449/S451/S454/T452 | PDLKKSRSASTIS |
| 83 | KCNA3_461_473_S468/S470/S473/T471 | EELRKARSNSTLS |
| 84 | KCNA6_504_516_S511/T515 | ANRERRPSYLPTP |
| 85 | KCNB1_489_501_S496/S499/S500/S501/T491/T494/T498 | KWTKRTLSETSSS |
| 86 | KIF11_919_931_S931/T923/T925/T926 | LDIPTGTTPQRKS |
| 87 | KIF2C_105_118_S106G/S109/S111/S115/S118/T112/T116 | EGLRSRSTRMSTVS |
| 88 | KPB1_1011_1023_S1018/S1020/S1023 | QVEFRRLSISAES |
| 89 | KPCB_19_31_A25S_S25 | RFARKGSLRQKNV |
| 90 | KPCB_626_639_T634 | AENFDRFFTRHPPV |
| 91 | LMNA_192_204_T199 | DAENRLQTMKEEL |
| 92 | LMNB1_16_28_S23/S28/T19/T20/T25 | GGPTTPLSPTRLS |
| 93 | MARCS_152_164_S159/S163 | KKKKKRFSFKKSF |
| 94 | MARCS_160_172_S163/S167/S170 | FKKSFKLSGFSFK |
| 95 | MBP_222_234_T229/T232 | HFFKNIVTPRTPP |
| 96 | MK10_214_226_S217/T216/T221/T226 | AGTSFMMTPYVVT |
| 97 | MP2K1_281_293_T286/T292 | GDAAETPPRPRTP |
| 98 | MP2K1_287_299_S298/S299/T292 | PPRPRTPGRPLSS |
| 99 | MPH6_140_152_T147 | EDENGDITPIKAK |
| 100 | MPIP3_208_220_S209/S214/S216 | RSGLYRSPSMPEN |
| 101 | MYBB_513_525_T515/T518/T520 | DNTPHTPTPFKNA |
| 102 | MYC_51_63_S62/T58 | KKFELLPTPPLSP |
| 103 | MYPC3_268_280_S269/S275/S274 | LSAFRRTSLAGGG |
| 104 | NCF1_296_308_S303/S304 | RGAPPRRSSIRNA |
| 105 | NCF1_321_333_S328 | QDAYRRNSVRFLQ |
| 106 | NEK2_172_184_S184/T175/T179 | FAKTFVGTPYYMS |
| 107 | NEK3_158_170_T161/T165 | FACTYVGTPYYVP |
| 108 | NFKB1_330_342_S337/S342/T341 | FVQLRRKSDLETS |
| 109 | NMDZ1_890_902_S890/S896/S897/S901/T900/T902 | SFKRRRSSKDTST |

TABLE 1-continued list of 142 peptide markers comprising phosphorylation sites used for determining the kinase activity, their sequence and SEQ ID NO The name of the peptide markers refers to the associated proteins and also refers to the start and the end position of the amino acid sequence.

| SEQ ID NO | Name | Sequence |
|---|---|---|
| 110 | NR4A1_344_356_S351 | GRRGRLPSKPKQP |
| 111 | NTRK3_824_836_T831 | LHALGKATPIYLD |
| 112 | P53_308_323_S313/S314/S315/T312 | LPNNTSSSPQPKKKPL |
| 113 | PDE5A_95_107_S102/S104/T96/T98 | GTPTRKISASEFD |
| 114 | PLEK_106_118_S113/S117/T114 | GQKFARKSTRRSI |
| 115 | PLM_76_88_S82/S83/S88/T79 | EEGTFRSSIRRLS |
| 116 | PP2AB_297_309_T301/T304 | EPHVTRRTPDYFL |
| 117 | PPR1A_28_40_T35/T38 | QIRRRRPTPATLV |
| 118 | PTK6_436_448_S442/S443/S446/T445 | ALRERLSSFTSYE |
| 119 | PTN12_32_44_S39/T40/T44 | FMRLRRLSTKYRT |
| 120 | PYGL_8_20_S15 | QEKRRQISIRGIV |
| 121 | RAB1A_187_199_S188/S194/T195 | KSNVKIQSTPVKQ |
| 122 | RADI_559_569_T564 | RDKYKTLRQIR |
| 123 | RAP1B_172_184_S179/S180 | PGKARKKSSCQLL |
| 124 | RB_242_254_S249/T252 | AVIPINGSPRTPR |
| 125 | RBL2_632_644_S639/T642 | DEICIAGSPLTPR |
| 126 | RBL2_655_667_S659/S662/S661/T664/T665 | GLGRSITSPTTLY |
| 127 | RBL2_959_971_S962/S965/S966/S971/T961 | DRTSRDSSPVMRS |
| 128 | REL_260_272_S267/S272 | KMQLRRPSDQEVS |
| 129 | RS6_228_240_S235/S236/S240 | IAKRRRLSSLRAS |
| 130 | RYR1_4317_4329_T4324 | VRRLRRLTAREAA |
| 131 | SCN7A_898_910_S905/S906 | KNGCRRGSSLGQI |
| 132 | SRC_413_425_T420 | LIEDNEYTARQGA |
| 133 | SRC8_CHICK_423_435_S426/S427/S435/T424 | KTPSSPVYQDAVS |
| 134 | STK6_283_295_S283/S284/T287/T288/T292 | SSRRTTLCGTLDY |
| 135 | STMN2_90_102_S97 | AAGERRKSQEAQV |
| 136 | TAU_524_536_S525/S527/S531/T529/T534 | GSRSRTPSLPTPP |
| 137 | TLE2_246_258_S249/T252/T253 | EPPSPATTPCGKV |
| 138 | VASP_150_162_S157 | EHIERRVSNAGGP |
| 139 | VASP_232_244_S239 | GAKLRKVSKQEEA |
| 140 | VASP_271_283_T278 | LARRRKATQVGEK |
| 141 | VIGLN_289_301_T295/T296/T297 | EEKKKKTTTIAVE |
| 142 | VTNC_390_402_S393/S397/T400 | NQNSRRPSRATWL |

It should further be noted that according to a preferred embodiment of the present invention the peptide markers as listed in Table 1 can be used as such for carrying out the methods according to the present invention. The present invention however also includes the use of analogs and combinations of these peptide markers for use in the method according to the present invention. The peptide marker analogs include peptide markers which show a sequence identity of more than 70%, preferably more than 80% and more preferably more than 90%.

In yet another embodiment, the present invention relates to a method according to the present invention wherein step (b) is replaced by steps (c) and (d) as provided below. The method according to the present invention may therefore comprise the steps of:

(a) measuring the kinase activity of a sample, obtained from the melanoma tumour from said patient, by contacting said sample with a set of protein kinase substrate comprising at least the peptide markers with SEQ ID NO 11, 27, 43, 52, 69, 113 and 124 in the presence and in the absence of a kinase inhibitor, thereby providing a phosphorylation profile of said sample in the presence of said kinase inhibitor and a phosphorylation profile of said sample in the absence of said kinase inhibitor; and, (c) comparing said phosphorylation profile of said sample in the presence of said kinase inhibitor with said phosphorylation profile of said sample in the absence of said kinase inhibitor, thereby determining a classifier parameter; and, (d) predicting the pharmacotherapeutical response of said patient to said medicament on the basis of said classifier parameter.

By establishing a classifier parameter for determining the prediction of pharmacotherapy response of the melanoma patient the method of the present invention provides a criterion for analysing the results obtained from the method of the present invention. This criterion enables a person to provide a prediction or prognosis on the basis of a single or limited number of data. The person providing the prediction or prognosis does not have to interpret an entire set of data, but rather bases his conclusion on the basis of a single or limited number of criteria.

The term "classifier parameter" as used herein represents a discriminating value which has been determined by establishing the phosphorylation profile in the presence and in the absence of a protein kinase inhibitor. Said discriminating value identifies the prediction of response of pharmacotherapy of melanoma patients. The classifier parameter includes information regarding the phosphorylation level of several protein kinase substrates. Classification is a procedure in which individual items are placed into groups based on quantitative information on one or more characteristics inherent in the items (e.g. phosphorylation levels or profiles of a sample) and based on a training set of previously labelled items (clinical response to a pharmacotherapy). The classifier parameter is calculated by applying a "classifier" to the measured phosphorylation levels of a sample. Based on the classifying parameter a sample is assigned to (or predicted to belong to) a class (predicting the pharmacotherapy response of said patient). The classifier has been previously determined by comparing samples which are known to belong to the respective relevant classes. For instance the classifier may be a mathematical function that uses information regarding the phosphorylation level of several protein kinase substrates which individual protein kinase substrates can be statistically weighted based on the measured phosphorylation level of a number of protein kinase substrates (or values derived from that). Several methods are known in the art for developing a classifier including the neural network (Multi-layer Perceptron), support vector machines, k-nearest neighbours, Gaussian mixture model, naive bayes, decision tree, RBF classifiers, random forest, discriminant analysis, linear discriminant analysis, quadratic discriminant analysis, discriminant analysis—principal component analysis, partial least squares discriminant analysis, generalized distance regression and elastic net classification. The classifier parameter determined in this manner is valid for the same experimental setup in future individual tests.

It is not relevant to give an exact threshold value for the classifier parameter. A relevant threshold value can be obtained by correlating the sensitivity and specificity and the sensitivity/specificity for any threshold value. A threshold value resulting in a high sensitivity results in a lower specificity and vice versa. If one wants to increase the positive predictive value of the test to determine whether melanoma patient will respond to targeted pharmacotherapy, then the threshold value of the test can be changed which as a consequence will decrease the negative predictive value of the test to determine whether melanoma patient will not respond to targeted pharmacotherapy. If one wants to increase the negative predictive value of the test to determine whether melanoma patient will not respond to targeted pharmacotherapy, then the threshold value can be changed in the opposite direction which as a consequence will decrease the positive predictive value of the test to determine whether melanoma patient will respond to targeted pharmacotherapy It is thus up to the diagnostic engineers to determine which level of positive predictive value/negative predictive value/sensitivity/specificity is desirable and how much loss in positive or negative predictive value is tolerable. The chosen threshold level could be dependent on other diagnostic parameters used in combination with the present method by the diagnostic engineers.

In yet another embodiment, the present invention relates to a method according to the present invention wherein said classifier parameter predicts the response of said patient to said medicament if said classifier parameter is above a first predetermined threshold level, and wherein said classifier parameter indicates non-response to said medicament of said patient if said classifier parameter is below a second predetermined threshold level.

According to another embodiment, the present invention relates to the method of the present invention wherein said differential phosphorylation level or said classifier parameter indicates a response, no-response or undetermined or intermediate prediction of said medicament or the effect of the targeted pharmacotherapy of said patient.

As used in the present application the prediction of response to targeted pharmacotherapy of melanoma patients is generally divided into two types of non-responders and responders and additionally some undetermined or intermediate responders. Whereas responders to a targeted pharmacotherapy will survive longer or have additional clinical benefits (e.g. improved quality of life, prolonged progression free survival, etc.) due to the treatment, the non-responders to a targeted pharmacotherapy will not benefit from the targeted pharmacotherapy. The method of the present invention specifically enables the distinction between responders and non-responders to a targeted pharmacotherapy.

The medicament as used in the method of the present invention can be any kind of chemical substance for instance used in the treatment, cure, prevention, or diagnosis of disease or used to otherwise enhance physical or mental well-being. Specifically said medicament can be a kinase inhibitor, and more preferably a protein kinase inhibitor and most preferably a small molecule protein kinase inhibitor.

As used herein, the term "protein kinase inhibitor" refers to a type of enzyme inhibitor which blocks the action of one or more protein kinases, hence they can be subdivided or characterised by peptides or proteins whose phosphorylation is inhibited.

More preferably the present invention relates to a method according to the present invention wherein said medicament is chosen from the list comprising Vemurafenib, Dabrafenib, Trametinib, AB1010 (Masitinib), AEB071 (Sotrastaurin), AG013736 (Axitinib), AMN107 (nilotinib), ARQ 197 (Tivantinib), ARRY-438162 (Binimetinib), AS703026 MSC1936369B (Pimasertib), AZD2644 (Selumetinib), BAY 43-9006 (Sorafenib), BEZ235 (Dactolisib), BKM120 (Buparlisib), BMS-908662, CEP-32496, E7050 (Golvatinib), E7080 (Lenvatinib), GDC-0973 (Cometinib), LEE011 (Ribociclib), LGX818 (Encorafenib), LY2801653, LY3009120, MLN2480, P276-00 (Riviciclib), PD-0325901, PLX3397, PLX3603, Vemurafenib, PLX7486, PLX8394, PX-866 (Sonolisib), RAF265, RO4987655, SAR260301, TAK-733, TK1258 (Dovitinib), XL184 (Cabozantinib), XL281 and/or analogs thereof, and wherein said kinase inhibitor is chosen from the list comprising Vemurafenib, Dabrafenib, Trametinib, AB1010 (Masitinib), AEB071 (Sotrastaurin), AG013736 (Axitinib), AMN107 (nilotinib), ARQ 197 (Tivantinib), ARRY-438162 (Binimetinib), AS703026 MSC1936369B (Pimasertib), AZD2644 (Selumetinib), BAY 43-9006 (Sorafenib), BEZ235 (Dactolisib), BKM120 (Buparlisib), BMS-908662, CEP-32496, E7050 (Golvatinib), E7080 (Lenvatinib), GDC-0973 (Cometinib), LEE011 (Ribociclib), LGX818 (Encorafenib), LY2801653, LY3009120, MLN2480, P276-00 (Riviciclib), PD-0325901, PLX3397, PLX3603, Vemurafenib, PLX7486, PLX8394, PX-866 (Sonolisib), RAF265, RO4987655, SAR260301, TAK-733, TK1258 (Dovitinib), XL184 (Cabozantinib), XL281 and/or analogs thereof. Preferably said medicament is chosen from the list comprising Vemurafenib, Dabrafenib and/or Trametinib, and said kinase inhibitor is chosen from the list comprising Vemurafenib, Dabrafenib and/or Trametinib. Preferably said medicament and said kinase inhibitor are identical and chosen from the list comprising Vemurafenib, Dabrafenib or Trametinib. The use of a kinase inhibitor during the method according to the invention allows for a better differentiation between patient groups. By choosing a kinase inhibitor identical to the medicament the response of a patient diagnosed with melanoma can be predicted.

According to a particular embodiment the present invention relates to a method according to the present invention wherein said medicament is chosen from the list comprising Vemurafenib, Dabrafenib, Trametinib, AB1010 (Masitinib), AEB071 (Sotrastaurin), AG013736 (Axitinib), AMN107 (nilotinib), ARQ 197 (Tivantinib), ARRY-438162 (Binimetinib), AS703026 MSC1936369B (Pimasertib), AZD2644 (Selumetinib), BAY 43-9006 (Sorafenib), BEZ235 (Dactolisib), BKM120 (Buparlisib), BMS-908662, CEP-32496, E7050 (Golvatinib), E7080 (Lenvatinib), GDC-0973 (Cometinib), LEE011 (Ribociclib), LGX818 (Encorafenib), LY2801653, LY3009120, MLN2480, P276-00 (Riviciclib), PD-0325901, PLX3397, PLX3603, Vemurafenib, PLX7486, PLX8394, PX-866 (Sonolisib), RAF265, RO4987655, SAR260301, TAK-733, TK1258 (Dovitinib), XL184 (Cabozantinib), XL281 and/or analogs thereof, and wherein said kinase inhibitor is chosen from the list comprising Vemurafenib, Dabrafenib, Trametinib, AB1010 (Masitinib), AEB071 (Sotrastaurin), AG013736 (Axitinib), AMN107 (nilotinib), ARQ 197 (Tivantinib), ARRY-438162 (Binimetinib), AS703026 MSC1936369B (Pimasertib), AZD2644 (Selumetinib), BAY 43-9006 (Sorafenib), BEZ235 (Dactolisib), BKM120 (Buparlisib), BMS-908662, CEP-32496, E7050 (Golvatinib), E7080 (Lenvatinib), GDC-0973 (Cometinib), LEE011 (Ribociclib), LGX818 (Encorafenib), LY2801653, LY3009120, MLN2480, P276-00 (Riviciclib), PD-0325901, PLX3397, PLX3603, Vemurafenib, PLX7486, PLX8394, PX-866 (Sonolisib), RAF265, RO4987655, SAR260301, TAK-733, TK1258 (Dovitinib), XL184 (Cabozantinib), XL281 and/or analogs thereof, with the proviso that said medicament and said kinase inhibitor are different compounds. Preferably said medicament is chosen from the list comprising Vemurafenib, Dabrafenib and/or Trametinib, and said kinase inhibitor is chosen from the list comprising Vemurafenib, Dabrafenib and/or Trametinib, with the proviso that said medicament and said kinase inhibitor are different compounds. More preferably said medicament is Vemurafenib and said kinase inhibitor is Dabrafenib. Preferably said medicament is Vemurafenib and said kinase inhibitor is Trametinib. Preferably said medicament is Dabrafenib and said kinase inhibitor is Vemurafenib. Preferably said medicament is Dabrafenib and said kinase inhibitor is Trametinib. Preferably said medicament is Trametinib and said kinase inhibitor is Vemurafenib. Preferably said medicament is Trametinib and said kinase inhibitor is Dabrafenib.

The use of different compounds as medicament and kinase inhibitor in the method according to the invention was also found to be beneficial. For instance the use of Dabrafenib as kinase inhibitor in the method according to the invention was found allow a prognosis of the outcome of the treatment with Vemurafenib as medicament. Indeed Vemurafenib responsive and Vemurafenib non-responsive patients were distinguished form each other using the method according to the invention with Dabrafenib as kinase inhibitor.

Another embodiment of the present invention relates to a method according to the present invention wherein said kinase substrates carrying phosphorylation sites are located or immobilized on a solid support, and preferably a porous solid support. Preferably said immobilized kinase substrates carrying phosphorylation sites will be immobilized proteins, peptides or peptide mimetics. In a preferred embodiment of the present invention peptides are immobilized on a solid support.

As used herein "peptide" refers to a short truncated protein generally consisting of 2 to 100, preferably 2 to 30, more preferably 5 to 30 and even more preferably 13 to 18 naturally occurring or synthetic amino acids which can also be further modified including covalently linking the peptide bonds of the alpha carboxyl group of a first amino acid and the alpha amino group of a second amino acid by eliminating a molecule of water. The amino acids can be either those naturally occurring amino acids or chemically synthesized variants of such amino acids or modified forms of these amino acids which can be altered from their basic chemical structure by addition of other chemical groups which can be found to be covalently attached to them in naturally occurring compounds.

As used herein "protein" refers to a polypeptide made of amino acids arranged in a linear chain and joined together by peptide bonds between the carboxyl and amino groups of adjacent amino acid residues.

As used herein "peptide mimetics" refers to organic compounds which are structurally similar to peptides and similar to the peptide sequences list in Table 1. The peptide mimetics are typically designed from existing peptides to alter the molecules characteristics. Improved characteristics can involve, for example improved stability such as resistance to enzymatic degradation, or enhanced biological activity, improved affinity by restricted preferred conformations and ease of synthesis. Structural modifications in the peptidomimetic in comparison to a peptide, can involve backbone modifications as well as side chain modification.

For measuring the kinase activity of the sample a large variety of methods and formats are known in the art. The kinase activity can for example be measured using ELISA and multiplex ELISA techniques, blotting methods, mass spectrometry, surface plasmon resonance, capillary electrophoresis, bead arrays, macroarrays, microarrays or any other method known in the art. Depending on the type of kinase activity measurement method the solid support on which the proteins, peptides or peptide mimetics are fixed may vary. Whereas in ELISA the protein kinase substrates are attached to the surface of the microtiterplates, in microarrays the protein kinase substrates are immobilized on and/or in the microarray substrate.

In a preferred embodiment of the present invention the protein kinase substrates are immobilized on an array, and preferably a microarray of protein kinase substrates wherein the protein kinase substrates are immobilized onto a solid support or another carrier. The immobilization can be either the attachment or adherence of two or more protein kinase substrate molecules to the surface of the carrier including attachment or adherence to the inner surface of said carrier in the case of e.g. a porous or flow-through solid support.

In a preferred embodiment of the present invention, the array of protein kinase substrates is a flow-through array. The flow-through array as used herein could be made of any carrier material having oriented through-going channels as are generally known in the art, such as for example described in PCT patent publication WO 01/19517. Typically the carrier is made from a metal oxide, glass, silicon oxide or cellulose. In a particular embodiment the carrier material is made of a metal oxide selected from the group consisting of zinc oxide, zirconium oxide, tin oxide, aluminium oxide, titanium oxide and thallium; in a more particular embodiment the metal oxide consists of aluminium oxide.

Accordingly, in a further embodiment of the present invention said array is a Pamchip®.

In a further embodiment, the present invention relates to a method according to the present invention wherein said peptide markers are serine and/or threonine containing peptides. In particular said peptide markers are substrates for serine and/or threonine kinases.

In a further embodiment, the present invention relates to a method according to the present invention wherein said solid support (microarray) comprises at least the peptide markers with SEQ ID NO 11, 27, 43, 52, 69, 113 and 124 as listed in Table 1 immobilized thereto.

In a further embodiment, the present invention relates to a method according to the present invention wherein said solid support (microarray) comprises each of the peptide as listed in Table 1 immobilized thereto.

In a further embodiment, the present invention relates to a method according to the present invention wherein said method is repeated for different concentration(s) of the kinase inhibitor, thereby generating phosphorylation profiles and differential phosphorylation levels in function of the kinase inhibitor concentration(s). In a further embodiment, the present invention relates to a method according to the present invention wherein said melanoma is a BRAF V600 mutation positive melanoma.

Phosphorylation levels can also be measured according to the invention, without the necessity to generate phosphorylation profiles thereof. Also for this embodiment, the amount and the type of peptides, proteins or peptide mimetics to be used is as described above.

The present invention also relates in another embodiment to a computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out the method according to the present invention.

The present invention further relates to a computer system comprising a processor, and a memory coupled to said processor and encoding one or more programs, wherein said one or more programs instruct the processor to carry out the methods according to the present invention.

The present invention also relates in another embodiment to a kit for determining the response of a patient diagnosed with melanoma, to a medicament, comprising at least one array comprising peptide markers with SEQ ID NO 11, 27, 43, 52, 69, 113 and 124, and a computer readable storage medium having recorded thereon one or more programs for carrying out the method according to the present invention.

The present invention further relates in yet another embodiment to the use of peptide markers with SEQ ID NO 11, 27, 43, 52, 69, 113 and 124 for predicting the response of a patient diagnosed with melanoma cancer to a medicament.

Unexpectedly, the present inventors showed that the use of at least seven specific peptide markers, namely peptide markers with SEQ ID NO 11, 27, 43, 52, 69, 113 and 124, in generating a phosphorylation inhibition profile sufficed to successfully differentiate responders and non-responders to targeted pharmacotherapy.

Since the present inventors have identified a surprisingly useful set of at least seven specific peptide markers, namely peptide markers with SEQ ID NO 11, 27, 43, 52, 69, 113 and 124, to be used in methods for accurately determining the prediction of response to a targeted pharmacotherapy of a patient suffering from melanoma, the skilled man may carry out any method as defined above wherein he measures the kinase activity of any of the peptide markers of Table 1. Also this method may be carried out using the amount and type of peptides, proteins or protein mimetics as defined above. The formats for carrying out these methods are also as for the methods described above.

The present invention is hereafter exemplified by the illustration of particular, non-limiting examples.

EXAMPLES

Example 1—Example Showing how Responders and Non-Responders to Targeted Pharmacotherapy can be Differentiated According to a Phosphorylation Inhibition Profile A clinical study was conducted using samples from melanoma patients which were not only mutated (BRAF mutation), but also treated with Vemurafenib. This allowed a comparison with the clinical responses.

In all the analyses, the first step is the lysis of the tumor tissue slices to extract the proteins. The kinase activity profiling was performed on a PamStation96 or a PamStation12 instrument that runs 96 (or 12) peptide microarrays. Each condition was run in multiple replicates. The small amount of material needed for one analysis (0.1 to 5 µg of total protein) allowed the additional testing of 4 concentrations of kinase inhibitors (concentration "a"=1 µM, "b"=10 µM, "c"=25 µM, "d"=0 µM). Besides the basal activity profiles, the same tumor samples were analysed in the presence and absence of the kinase inhibitor Dabrafenib. The degree of inhibition versus control (DMSO) was determined for each peptide on the peptide microarray. The tumor samples of the four melanoma patients who clinically responded to the Vemurafenib medicament treatment are indicated as "R1", "R2", "R3" and "R4" and the tumor samples of the melanoma patients who clinically did not response to Vemurafenib medicament treatment are indicated as "NR1", "NR2", "NR3". In FIG. 1 the residual kinase activity on the peptides markers with Seq ID No 11, 27, 43, 52, 69, 113 and 124 are shown in grey scale (white no inhibition by Dabrafenib, black 100% inhibition by Dabrafenib compared to the control without Dabrafenib "d").

FIG. 1 shows that the method according to the invention using Dabrafenib as kinase inhibitor allows a good prediction of the treatment outcome of patients treated with Vemurafenib.

Using Dabrafenib as kinase inhibitor in the method according to the present invention it was possible to divide patients which are either responsive or non-responsive to a treatment with Vemurafenib. In particular SEQ ID NO 11, 27, 43, 52, 69, 113 and 124 as listed in table 1 were identified as key biomarkers for the differentiation between responsive and non-responsive patients.

It should be noted, that all the patients in this study were positive in the classical BRAF mutation test. In other words, according to that existing standard genomic test all those patients were expected to respond to therapy, which was wrong. The method according to the present invention improves the prediction significantly, leading to less overtreatment and an earlier possibility to switch to (or start with) immunotherapy.

The invention claimed is:

1. A method for predicting the response of a patient diagnosed with BRAF-activating mutation positive melanoma cancer, to a medicament, wherein said medicament is a first inhibitor of BRAF kinase or MEK, comprising the steps of:
   (a) contacting a sample obtained from a melanoma tumor, or a metastasis thereof, from the patient with a set of protein kinase substrates comprising at least peptide markers SEQ ID Nos: 11, 27, 43, 52, 69, 113 and 124 in the presence and in the absence of a second inhibitor of BRAF kinase or MEK; wherein said first and said second inhibitor of BRAF kinase or MEK are identical or different compounds;
   (b) measuring phosphorylation of one or more phosphorylation sites present on the peptide markers of the set of protein kinase substrates to obtain a phosphorylation profile of said sample in the presence of said second inhibitor of BRAF kinase or MEK and a phosphorylation profile of said sample in the absence of said second inhibitor of BRAF kinase or MEK; and
   (c) determining from said phosphorylation profiles in the presence and in the absence of said second inhibitor of BRAF kinase or MEK a differential phosphorylation level, said differential phosphorylation level predicting the response of said patient to said medicament; wherein a decreased phosphorylation of the one or more phosphorylation sites present on the peptide markers of the set of protein kinase substrates in the presence of said second inhibitor of BRAF or MEK is predictive of a response of said patient to said medicament.

2. The method according to claim 1, wherein the set of protein kinase substrates further comprises one or more peptide marker SEQ ID NOs selected from the group consisting of: SEQ ID NOs:1-10, 12-26, 28-42, 44-51, 53-68, 70-112, 114-123, and 125-142.

3. The method according to claim 1, wherein said medicament is selected from the group consisting of Vemurafenib, Dabrafenib, Trametinib, AEB071 (Sotrastaurin), ARRY-438162 (Binimetinib), AS703026 MSC1936369B (Pimasertib), AZD2644 (Selumetinib), BAY 43-9006 (Sorafenib), BMS-908662, CEP-32496, GDC-0973 (Cometinib), LGX818 (Encorafenib), LY3009120, MLN2480, PD-0325901, PLX3603, PLX7486, PLX8394, RAF265, RO4987655, TAK-733 and XL281; and wherein said kinase inhibitor is selected from the group consisting of Vemurafenib, Dabrafenib, Trametinib, AEB071 (Sotrastaurin), ARRY-438162 (Binimetinib), AS703026 MSC1936369B (Pimasertib), AZD2644 (Selumetinib), BAY 43-9006 (Sorafenib), BMS-908662, CEP-32496, GDC-0973 (Cometinib), LGX818 (Encorafenib), LY3009120, MLN2480, PD-0325901, PLX3603, PLX7486, PLX8394, RAF265, RO4987655, TAK-733 and XL281, or analogs thereof.

4. The method according to claim 3, wherein said medicament and said second inhibitor of BRAF kinase or MEK are different compounds.

5. The method according to claim 3, wherein said medicament is Vemurafenib and said second inhibitor of BRAF kinase or MEK is Dabrafenib.

6. The method according to claim 1, wherein said one or more phosphorylation sites are present on proteins, peptides or peptide mimetics comprising the peptide markers immobilized on a solid support.

7. The method of claim 6, wherein the solid support is a porous solid support.

8. The method according to claim 1, wherein the peptide markers are serine and/or threonine containing peptides.

9. The method according to claim 1, further comprising repeating one or more times steps (a), (b) and (c), wherein in step (a) the sample is contacted with the set of protein kinase substrates in the presence and in the absence of the second inhibitor of BRAF kinase or MEK wherein the concentration of inhibitor of BRAF kinase or MEK is different from the concentration of the inhibitor of BRAF kinase or MEK used in first execution of step (a), thereby generating phosphorylation profiles and differential phosphorylation levels in function of the inhibitor concentration of the inhibitor of BRAF kinase or MEK.

10. The method according to claim 1, wherein said melanoma is a BRAF V600 mutation positive melanoma.

11. A method of treating a patient diagnosed with BRAF-activating mutation positive melanoma cancer comprising receiving a prediction of the response of the patient to a medicament, wherein the prediction is performed by the method of claim 1, and treating the patient based on the prediction of the response of the patient to the medicament;
wherein said medicament is a first inhibitor of BRAF kinase or MEK, and wherein said medicament is selected from the group consisting of Vemurafenib, Dabrafenib, Trametinib, AEB071 (Sotrastaurin), ARRY-438162 (Binimetinib), AS703026 MSC1936369B (Pimasertib), AZD2644 (Selumetinib), BAY 43-9006 (Sorafenib), BMS-908662, CEP-32496, GDC-0973 (Cometinib), LGX818 (Encorafenib), LY3009120, MLN2480, PD-0325901, PLX3603, PLX7486, PLX8394, RAF265, RO4987655, TAK-733 and XL281; and
wherein the patient diagnosed with BRAF-activating mutation positive melanoma cancer is treated with said medicament when it is predicted that the patient will clinically respond to the medicament; and wherein the patient diagnosed with BRAF-activating mutation positive melanoma cancer is treated by treatment options different from said medicament, including surgery, chemotherapy, targeted therapy, immunotherapy and radiation therapy, when it is predicted that the patient will not clinically respond to the medicament.

* * * * *

SEQUENCE LISTING

<160> NUMBER OF SEQ ID NOS: 142

<210> SEQ ID NO 1
<211> LENGTH: 13
<212> TYPE: PRT
<213> ORGANISM: Artificial Sequence
<220> FEATURE:
<223> OTHER INFORMATION: Peptide

<400> SEQUENCE: 1

Val Arg Met Arg His Leu Ser Gln Glu Phe Gly Trp Leu
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Peptide

<400> SEQUENCE: 2

Lys Arg Ser Leu Ala Phe Glu Glu Gly Ser Gln Ser Thr
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Peptide

<400> SEQUENCE: 3

Arg Glu Leu Arg Arg Met Ser Asp Glu Phe Val Asp Ser
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Peptide

<400> SEQUENCE: 4

Ile Arg Ser Arg His Ser Ser Tyr Pro Ala Gly Thr Glu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Peptide

<400> SEQUENCE: 5

Phe Arg Gly Arg Ser Arg Ser Ala Pro Pro Asn Leu Trp
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Peptide

<400> SEQUENCE: 6

Glu Lys Ala Val Leu Thr Ser Gln Lys Ser Ser Glu Tyr
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Peptide

<400> SEQUENCE: 7

Ala Ser Gly Tyr Ile Ser Ser Leu Glu Tyr Pro Arg Ser
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Peptide

<400> SEQUENCE: 8

Gly Arg Lys Arg Arg Gln Thr Ser Met Thr Asp Phe Tyr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Peptide

<400> SEQUENCE: 9

Ile Arg Lys Arg Pro Ala Thr Asp Asp Ser Ser Thr Gln
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Peptide

<400> SEQUENCE: 10

Ala Ile Leu Arg Arg Pro Thr Ser Pro Val Ser Arg Glu
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Peptide

<400> SEQUENCE: 11

Arg Thr Arg Thr Asp Ser Tyr Ser Ala Gly Gln Ser Val
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Peptide

<400> SEQUENCE: 12

Val Pro Glu Ser Ile His Ser Phe Ile Gly Asp Gly Leu
1               5                   10

```
<210> SEQ ID NO 13
<211> LENGTH: 13
<212> TYPE: PRT
<213> ORGANISM: Artificial Sequence
<220> FEATURE:
<223> OTHER INFORMATION: Peptide

<400> SEQUENCE: 13

Thr Ala Thr Lys Ser Gly Ser Thr Thr Lys Asn Arg Phe
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Peptide

<400> SEQUENCE: 14

Leu Asp Asp Arg His Asp Ser Gly Leu Asp Ser Met Lys
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Peptide

<400> SEQUENCE: 15

Leu Asp Gln Gly Ser Leu Ala Thr Ser Phe Val Gly Thr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Peptide

<400> SEQUENCE: 16

Gln Leu Met Ser Gln Pro Ser Thr Ala Ser Asn Ser Leu
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Peptide

<400> SEQUENCE: 17

Gln Leu Phe Arg Gly Phe Ser Phe Val Ala Thr Gly Leu
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Peptide

<400> SEQUENCE: 18

Gly Phe His Pro Arg Ser Ser Gln Gly Ala Thr Gln
1               5                   10
```

```
<210> SEQ ID NO 19
<211> LENGTH: 13
<212> TYPE: PRT
<213> ORGANISM: Artificial Sequence
<220> FEATURE:
<223> OTHER INFORMATION: Peptide

<400> SEQUENCE: 19

Phe Thr Gln Arg Gln Asn Ser Ala Pro Ala Arg Met Leu
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Peptide

<400> SEQUENCE: 20

Ser Arg Ile Arg Thr Gln Ser Phe Ser Leu Gln Glu Arg
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Peptide

<400> SEQUENCE: 21

Pro Pro Leu Ser Gln Glu Thr Phe Ser Asp Leu Trp Lys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Peptide

<400> SEQUENCE: 22

Ser Met Val Arg Thr Gln Thr Glu Ser Ser Thr Pro Pro
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Peptide

<400> SEQUENCE: 23

Thr Arg Thr Gln Glu Gly Ser Leu Ser Ala Arg Trp Pro
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Peptide

<400> SEQUENCE: 24

Gln Arg Gln Arg Ser Thr Ser Thr Pro Asn Val His Met
1               5                   10

<210> SEQ ID NO 25
```

```
<211> LENGTH: 13
<212> TYPE: PRT
<213> ORGANISM: Artificial Sequence
<220> FEATURE:
<223> OTHER INFORMATION: Peptide

<400> SEQUENCE: 25

Ser Phe Glu Thr Gln Arg Thr Pro Arg Lys Ser Asn Leu
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Peptide

<400> SEQUENCE: 26

Thr Arg Pro Pro Thr Leu Ser Pro Ile Pro His Ile Pro
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Peptide

<400> SEQUENCE: 27

Asn Ile Tyr Ile Ser Pro Leu Lys Ser Pro Tyr Lys Ile
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Peptide

<400> SEQUENCE: 28

Arg Arg Lys Arg Lys Pro Ser Thr Ser Asp Asp Ser Asp
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Peptide

<400> SEQUENCE: 29

Phe Ile Gly Arg Arg Gln Ser Leu Ile Glu Asp Ala Arg
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Peptide

<400> SEQUENCE: 30

Gln His Val Arg Ala His Ser Ser Pro Ala Ser Leu Gln
1               5                   10

<210> SEQ ID NO 31
<211> LENGTH: 13
```

```
<212> TYPE: PRT
<213> ORGANISM: Artificial Sequence
<220> FEATURE:
<223> OTHER INFORMATION: Peptide

<400> SEQUENCE: 31

Cys Asn Lys Ala Phe Arg Asp Thr Phe Arg Leu Leu Leu
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Peptide

<400> SEQUENCE: 32

Lys Ile Pro Lys Arg Pro Gly Ser Val His Arg Thr Pro
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Peptide

<400> SEQUENCE: 33

Cys Asn Ala Thr Phe Lys Lys Thr Phe Arg His Leu Leu
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Peptide

<400> SEQUENCE: 34

Cys Tyr Ala Leu Cys Asn Arg Thr Phe Arg Lys Thr Phe
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Peptide

<400> SEQUENCE: 35

Cys Asn Arg Thr Phe Arg Lys Thr Phe Lys Met Leu Leu
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Peptide

<400> SEQUENCE: 36

Gly Ser Pro Ser Lys Ser Pro Ser Lys Lys Lys Lys Lys
1               5                   10

<210> SEQ ID NO 37
<211> LENGTH: 13
<212> TYPE: PRT
```

```
<213> ORGANISM: Artificial Sequence
<220> FEATURE:
<223> OTHER INFORMATION: Peptide

<400> SEQUENCE: 37

Lys Lys Lys Phe Arg Thr Pro Ser Phe Leu Lys Lys Ser
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Peptide

<400> SEQUENCE: 38

Glu Leu Leu Cys Leu Arg Arg Ser Ser Leu Lys Ala Tyr
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Peptide

<400> SEQUENCE: 39

Lys Asp Gly Ala Thr Met Lys Thr Phe Cys Gly Thr Pro
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Peptide

<400> SEQUENCE: 40

Ala Gly Glu Arg Arg Lys Gly Thr Asp Val Asn Val Phe
1               5                   10

<210> SEQ ID NO 41
<211> LENGTH: 15
<212> TYPE: PRT
<213> ORGANISM: Artificial Sequence
<220> FEATURE:
<223> OTHER INFORMATION: Peptide

<400> SEQUENCE: 41

Gly Leu Arg Arg Trp Ser Leu Gly Gly Leu Arg Arg Trp Ser Leu
1               5                   10                  15

<210> SEQ ID NO 42
<211> LENGTH: 13
<212> TYPE: PRT
<213> ORGANISM: Artificial Sequence
<220> FEATURE:
<223> OTHER INFORMATION: Peptide

<400> SEQUENCE: 42

Val Ala Asp Gln Thr Pro Thr Pro Thr Arg Phe Leu Lys
1               5                   10

<210> SEQ ID NO 43
<211> LENGTH: 13
<212> TYPE: PRT
<213> ORGANISM: Artificial Sequence
```

```
<220> FEATURE:
<223> OTHER INFORMATION: Peptide

<400> SEQUENCE: 43

Glu Arg Ser Lys Thr Val Thr Ser Phe Tyr Asn Gln Ser
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Peptide

<400> SEQUENCE: 44

Leu Glu Asp Ile Lys Arg Leu Thr Pro Arg Phe Thr Leu
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Peptide

<400> SEQUENCE: 45

Ala Ser Leu Gly Arg Arg Ala Ser Phe His Leu Glu Cys
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Peptide

<400> SEQUENCE: 46

His Gln Arg Arg Lys Tyr Arg Ser Asn Lys Gly Glu Ser
1               5                   10

<210> SEQ ID NO 47
<211> LENGTH: 16
<212> TYPE: PRT
<213> ORGANISM: Artificial Sequence
<220> FEATURE:
<223> OTHER INFORMATION: Peptide

<400> SEQUENCE: 47

Gly Ile Pro Ile Arg Val Tyr Thr His Glu Val Val Thr Leu Trp Tyr
1               5                   10                  15

<210> SEQ ID NO 48
<211> LENGTH: 13
<212> TYPE: PRT
<213> ORGANISM: Artificial Sequence
<220> FEATURE:
<223> OTHER INFORMATION: Peptide

<400> SEQUENCE: 48

Gly Ser Pro Asn Arg Ala Tyr Thr His Gln Val Val Thr
1               5                   10

<210> SEQ ID NO 49
<211> LENGTH: 14
<212> TYPE: PRT
<213> ORGANISM: Artificial Sequence
<220> FEATURE:
```

<223> OTHER INFORMATION: Peptide

<400> SEQUENCE: 49

Met Gly Pro Arg Arg Arg Ser Arg Lys Pro Glu Ala Pro Arg
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Peptide

<400> SEQUENCE: 50

Glu Pro Leu Glu Arg Arg Leu Ser Leu Val Pro Asp Ser
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Peptide

<400> SEQUENCE: 51

Leu Gln Ala Arg Arg Arg Gln Ser Val Leu Asn Leu Met
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Peptide

<400> SEQUENCE: 52

Gln Cys Ala Leu Cys Arg Arg Ser Thr Thr Asp Cys Gly
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Peptide

<400> SEQUENCE: 53

Asp Met Lys Val Arg Lys Ser Ser Thr Pro Glu Glu Val
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Peptide

<400> SEQUENCE: 54

Glu Ile Leu Ser Arg Arg Pro Ser Tyr Arg Lys Ile Leu
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Peptide

<400> SEQUENCE: 55

Asn Ile His Leu Glu Lys Lys Tyr Val Arg Arg Asp Ser
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Peptide

<400> SEQUENCE: 56

Ile Ser Ser Val Pro Thr Pro Ser Pro Leu Gly Pro Leu
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Peptide

<400> SEQUENCE: 57

His Phe Asp Glu Arg Asp Lys Thr Ser Arg Asn Met Arg
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Peptide

<400> SEQUENCE: 58

Arg Ser Gly Ser Arg Arg Gly Ser Phe Asp Ala Thr Gly
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Peptide

<400> SEQUENCE: 59

Leu Leu Pro Thr His Thr Leu Thr Pro Val Leu Leu Thr
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Peptide

<400> SEQUENCE: 60

Ile Ser Val Asp Gly Leu Ser Thr Pro Val Val Leu Ser
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Peptide

```
<400> SEQUENCE: 61

Leu Leu Asn Lys Arg Arg Gly Ser Val Pro Ile Leu Arg
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Peptide

<400> SEQUENCE: 62

Gln Gln Lys Ile Arg Lys Tyr Thr Met Arg Arg Leu Leu
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Peptide

<400> SEQUENCE: 63

Gly Glu Ala Gly Gly Pro Leu Thr Pro Arg Arg Val Ser
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Peptide

<400> SEQUENCE: 64

Gly Gly Arg Glu Arg Leu Ala Ser Thr Asn Asp Lys Gly
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Peptide

<400> SEQUENCE: 65

Asn Pro Leu Met Arg Arg Asn Ser Val Thr Pro Leu Ala
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Peptide

<400> SEQUENCE: 66

Glu Phe Pro Ser Arg Gly Lys Ser Ser Ser Tyr Ser Lys
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Peptide

<400> SEQUENCE: 67
```

```
Gln Ser Arg Pro Arg Ser Cys Thr Trp Pro Leu Gln Arg
1               5                   10
```

<210> SEQ ID NO 68
<211> LENGTH: 13
<212> TYPE: PRT
<213> ORGANISM: Artificial Sequence
<220> FEATURE:
<223> OTHER INFORMATION: Peptide

<400> SEQUENCE: 68

```
Ser Arg Leu Arg Arg Arg Ala Ser Gln Leu Lys Ile Thr
1               5                   10
```

<210> SEQ ID NO 69
<211> LENGTH: 13
<212> TYPE: PRT
<213> ORGANISM: Artificial Sequence
<220> FEATURE:
<223> OTHER INFORMATION: Peptide

<400> SEQUENCE: 69

```
Gln Ser Lys Val Pro Phe Arg Ser Arg Ser Pro Ser Glu
1               5                   10
```

<210> SEQ ID NO 70
<211> LENGTH: 13
<212> TYPE: PRT
<213> ORGANISM: Artificial Sequence
<220> FEATURE:
<223> OTHER INFORMATION: Peptide

<400> SEQUENCE: 70

```
Pro Lys Leu Gly Arg Arg His Ser Met Glu Asn Met Glu
1               5                   10
```

<210> SEQ ID NO 71
<211> LENGTH: 13
<212> TYPE: PRT
<213> ORGANISM: Artificial sequence
<220> FEATURE:
<223> OTHER INFORMATION: Peptide

<400> SEQUENCE: 71

```
Phe Met Ser Ser Arg Arg Gln Ser Val Leu Val Lys Ser
1               5                   10
```

<210> SEQ ID NO 72
<211> LENGTH: 13
<212> TYPE: PRT
<213> ORGANISM: Artificial Sequence
<220> FEATURE:
<223> OTHER INFORMATION: Peptide

<400> SEQUENCE: 72

```
Lys Lys Pro Arg Arg Lys Asp Thr Pro Ala Leu His Ile
1               5                   10
```

<210> SEQ ID NO 73
<211> LENGTH: 13
<212> TYPE: PRT
<213> ORGANISM: Artificial Sequence
<220> FEATURE:
<223> OTHER INFORMATION: Peptide

<400> SEQUENCE: 73

```
Met Leu Arg Gly Arg Ser Leu Ser Val Thr Ser Leu Gly
1               5                   10
```

<210> SEQ ID NO 74
<211> LENGTH: 14
<212> TYPE: PRT
<213> ORGANISM: Artificial Sequence
<220> FEATURE:
<223> OTHER INFORMATION: Peptide

<400> SEQUENCE: 74

```
Gly Lys Lys Arg Lys Arg Ser Arg Lys Glu Ser Tyr Ser Ile
1               5                   10
```

<210> SEQ ID NO 75
<211> LENGTH: 16
<212> TYPE: PRT
<213> ORGANISM: Artificial Sequence
<220> FEATURE:
<223> OTHER INFORMATION: Peptide

<400> SEQUENCE: 75

```
Arg Thr Lys Gln Thr Ala Arg Lys Ser Thr Gly Gly Lys Ala Pro Arg
1               5                   10                  15
```

<210> SEQ ID NO 76
<211> LENGTH: 13
<212> TYPE: PRT
<213> ORGANISM: Artificial Sequence
<220> FEATURE:
<223> OTHER INFORMATION: Peptide

<400> SEQUENCE: 76

```
Leu Glu His Val Thr Arg Arg Thr Leu Ser Met Asp Lys
1               5                   10
```

<210> SEQ ID NO 77
<211> LENGTH: 13
<212> TYPE: PRT
<213> ORGANISM: Artificial Sequence
<220> FEATURE:
<223> OTHER INFORMATION: Peptide

<400> SEQUENCE: 77

```
Ser Arg Phe Asn Arg Arg Val Ser Val Cys Ala Glu Thr
1               5                   10
```

<210> SEQ ID NO 78
<211> LENGTH: 13
<212> TYPE: PRT
<213> ORGANISM: Artificial Sequence
<220> FEATURE:
<223> OTHER INFORMATION: Peptide

<400> SEQUENCE: 78

```
Asn Arg Phe Thr Arg Arg Ala Ser Val Cys Ala Glu Ala
1               5                   10
```

<210> SEQ ID NO 79
<211> LENGTH: 15
<212> TYPE: PRT
<213> ORGANISM: Artificial Sequence
<220> FEATURE:
<223> OTHER INFORMATION: Peptide

<400> SEQUENCE: 79

```
Val Lys Gly Arg Thr Trp Thr Leu Cys Gly Thr Pro Glu Tyr Leu
```

-continued

```
<210> SEQ ID NO 80
<211> LENGTH: 12
<212> TYPE: PRT
<213> ORGANISM: Artificial Sequence
<220> FEATURE:
<223> OTHER INFORMATION: Peptide

<400> SEQUENCE: 80

Val Ala Ser Met Met His Arg Gln Glu Thr Val Glu
1               5                  10

<210> SEQ ID NO 81
<211> LENGTH: 13
<212> TYPE: PRT
<213> ORGANISM: Artificial Sequence
<220> FEATURE:
<223> OTHER INFORMATION: Peptide

<400> SEQUENCE: 81

Asp Ser Asp Leu Ser Arg Arg Ser Ser Ser Thr Met Ser
1               5                  10

<210> SEQ ID NO 82
<211> LENGTH: 13
<212> TYPE: PRT
<213> ORGANISM: Artificial Sequence
<220> FEATURE:
<223> OTHER INFORMATION: Peptide

<400> SEQUENCE: 82

Pro Asp Leu Lys Lys Ser Arg Ser Ala Ser Thr Ile Ser
1               5                  10

<210> SEQ ID NO 83
<211> LENGTH: 13
<212> TYPE: PRT
<213> ORGANISM: Artificial Sequence
<220> FEATURE:
<223> OTHER INFORMATION: Peptide

<400> SEQUENCE: 83

Glu Glu Leu Arg Lys Ala Arg Ser Asn Ser Thr Leu Ser
1               5                  10

<210> SEQ ID NO 84
<211> LENGTH: 13
<212> TYPE: PRT
<213> ORGANISM: Artificial Sequence
<220> FEATURE:
<223> OTHER INFORMATION: Peptide

<400> SEQUENCE: 84

Ala Asn Arg Glu Arg Arg Pro Ser Tyr Leu Pro Thr Pro
1               5                  10

<210> SEQ ID NO 85
<211> LENGTH: 13
<212> TYPE: PRT
<213> ORGANISM: Artificial Sequence
<220> FEATURE:
<223> OTHER INFORMATION: Peptide

<400> SEQUENCE: 85

Lys Trp Thr Lys Arg Thr Leu Ser Glu Thr Ser Ser Ser
1               5                  10
```

```
<210> SEQ ID NO 86
<211> LENGTH: 13
<212> TYPE: PRT
<213> ORGANISM: Artificial Sequence
<220> FEATURE:
<223> OTHER INFORMATION: Peptide

<400> SEQUENCE: 86

Leu Asp Ile Pro Thr Gly Thr Thr Pro Gln Arg Lys Ser
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Peptide

<400> SEQUENCE: 87

Glu Gly Leu Arg Ser Arg Ser Thr Arg Met Ser Thr Val Ser
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Peptide

<400> SEQUENCE: 88

Gln Val Glu Phe Arg Arg Leu Ser Ile Ser Ala Glu Ser
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Peptide

<400> SEQUENCE: 89

Arg Phe Ala Arg Lys Gly Ser Leu Arg Gln Lys Asn Val
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Peptide

<400> SEQUENCE: 90

Ala Glu Asn Phe Asp Arg Phe Phe Thr Arg His Pro Pro Val
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Peptide

<400> SEQUENCE: 91

Asp Ala Glu Asn Arg Leu Gln Thr Met Lys Glu Glu Leu
1               5                   10
```

```
<210> SEQ ID NO 92
<211> LENGTH: 13
<212> TYPE: PRT
<213> ORGANISM: Artificial Sequence
<220> FEATURE:
<223> OTHER INFORMATION: Peptide

<400> SEQUENCE: 92

Gly Gly Pro Thr Thr Pro Leu Ser Pro Thr Arg Leu Ser
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Peptide

<400> SEQUENCE: 93

Lys Lys Lys Lys Lys Arg Phe Ser Phe Lys Lys Ser Phe
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Peptide

<400> SEQUENCE: 94

Phe Lys Lys Ser Phe Lys Leu Ser Gly Phe Ser Phe Lys
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Peptide

<400> SEQUENCE: 95

His Phe Phe Lys Asn Ile Val Thr Pro Arg Thr Pro Pro
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Peptide

<400> SEQUENCE: 96

Ala Gly Thr Ser Phe Met Met Thr Pro Tyr Val Val Thr
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Peptide

<400> SEQUENCE: 97

Gly Asp Ala Ala Glu Thr Pro Pro Arg Pro Arg Thr Pro
1               5                   10
```

```
<210> SEQ ID NO 98
<211> LENGTH: 13
<212> TYPE: PRT
<213> ORGANISM: Artificial Sequence
<220> FEATURE:
<223> OTHER INFORMATION: Peptide

<400> SEQUENCE: 98

Pro Pro Arg Pro Arg Thr Pro Gly Arg Pro Leu Ser Ser
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Peptide

<400> SEQUENCE: 99

Glu Asp Glu Asn Gly Asp Ile Thr Pro Ile Lys Ala Lys
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Peptide

<400> SEQUENCE: 100

Arg Ser Gly Leu Tyr Arg Ser Pro Ser Met Pro Glu Asn
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Peptide

<400> SEQUENCE: 101

Asp Asn Thr Pro His Thr Pro Thr Pro Phe Lys Asn Ala
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Peptide

<400> SEQUENCE: 102

Lys Lys Phe Glu Leu Leu Pro Thr Pro Pro Leu Ser Pro
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Peptide

<400> SEQUENCE: 103

Leu Ser Ala Phe Arg Arg Thr Ser Leu Ala Gly Gly Gly
1               5                   10

<210> SEQ ID NO 104
```

```
<211> LENGTH: 13
<212> TYPE: PRT
<213> ORGANISM: Artificial Sequence
<220> FEATURE:
<223> OTHER INFORMATION: Peptide

<400> SEQUENCE: 104

Arg Gly Ala Pro Pro Arg Arg Ser Ser Ile Arg Asn Ala
1               5                   10

<210> SEQ ID NO 105
<211> LENGTH: 13
<212> TYPE: PRT
<213> ORGANISM: Artificial Sequence
<220> FEATURE:
<223> OTHER INFORMATION: Peptide

<400> SEQUENCE: 105

Gln Asp Ala Tyr Arg Arg Asn Ser Val Arg Phe Leu Gln
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Peptide

<400> SEQUENCE: 106

Phe Ala Lys Thr Phe Val Gly Thr Pro Tyr Tyr Met Ser
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Peptide

<400> SEQUENCE: 107

Phe Ala Cys Thr Tyr Val Gly Thr Pro Tyr Tyr Val Pro
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Peptide

<400> SEQUENCE: 108

Phe Val Gln Leu Arg Arg Lys Ser Asp Leu Glu Thr Ser
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Peptide

<400> SEQUENCE: 109

Ser Phe Lys Arg Arg Arg Ser Ser Lys Asp Thr Ser Thr
1               5                   10

<210> SEQ ID NO 110
<211> LENGTH: 13
```

```
<212> TYPE: PRT
<213> ORGANISM: Artificial Sequence
<220> FEATURE:
<223> OTHER INFORMATION: Peptide

<400> SEQUENCE: 110

Gly Arg Arg Gly Arg Leu Pro Ser Lys Pro Lys Gln Pro
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Peptide

<400> SEQUENCE: 111

Leu His Ala Leu Gly Lys Ala Thr Pro Ile Tyr Leu Asp
1               5                   10

<210> SEQ ID NO 112
<211> LENGTH: 16
<212> TYPE: PRT
<213> ORGANISM: Artificial Sequence
<220> FEATURE:
<223> OTHER INFORMATION: Peptide

<400> SEQUENCE: 112

Leu Pro Asn Asn Thr Ser Ser Ser Pro Gln Pro Lys Lys Lys Pro Leu
1               5                   10                  15

<210> SEQ ID NO 113
<211> LENGTH: 13
<212> TYPE: PRT
<213> ORGANISM: Artificial Sequence
<220> FEATURE:
<223> OTHER INFORMATION: Peptide

<400> SEQUENCE: 113

Gly Thr Pro Thr Arg Lys Ile Ser Ala Ser Glu Phe Asp
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Peptide

<400> SEQUENCE: 114

Gly Gln Lys Phe Ala Arg Lys Ser Thr Arg Arg Ser Ile
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Peptide

<400> SEQUENCE: 115

Glu Glu Gly Thr Phe Arg Ser Ser Ile Arg Arg Leu Ser
1               5                   10

<210> SEQ ID NO 116
<211> LENGTH: 13
<212> TYPE: PRT
```

```
<213> ORGANISM: Artificial Sequence
<220> FEATURE:
<223> OTHER INFORMATION: Peptide

<400> SEQUENCE: 116

Glu Pro His Val Thr Arg Arg Thr Pro Asp Tyr Phe Leu
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Peptide

<400> SEQUENCE: 117

Gln Ile Arg Arg Arg Arg Pro Thr Pro Ala Thr Leu Val
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Peptide

<400> SEQUENCE: 118

Ala Leu Arg Glu Arg Leu Ser Ser Phe Thr Ser Tyr Glu
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Peptide

<400> SEQUENCE: 119

Phe Met Arg Leu Arg Arg Leu Ser Thr Lys Tyr Arg Thr
1               5                   10

<210> SEQ ID NO 120
<211> LENGTH: 13
<212> TYPE: PRT
<213> ORGANISM: Artificial Sequence
<220> FEATURE:
<223> OTHER INFORMATION: Peptide

<400> SEQUENCE: 120

Gln Glu Lys Arg Arg Gln Ile Ser Ile Arg Gly Ile Val
1               5                   10

<210> SEQ ID NO 121
<211> LENGTH: 13
<212> TYPE: PRT
<213> ORGANISM: Artificial Sequence
<220> FEATURE:
<223> OTHER INFORMATION: Peptide

<400> SEQUENCE: 121

Lys Ser Asn Val Lys Ile Gln Ser Thr Pro Val Lys Gln
1               5                   10

<210> SEQ ID NO 122
<211> LENGTH: 11
<212> TYPE: PRT
<213> ORGANISM: Artificial Sequence
```

```
<220> FEATURE:
<223> OTHER INFORMATION: Peptide

<400> SEQUENCE: 122

Arg Asp Lys Tyr Lys Thr Leu Arg Gln Ile Arg
1               5                   10

<210> SEQ ID NO 123
<211> LENGTH: 13
<212> TYPE: PRT
<213> ORGANISM: Artificial Sequence
<220> FEATURE:
<223> OTHER INFORMATION: Peptide

<400> SEQUENCE: 123

Pro Gly Lys Ala Arg Lys Lys Ser Ser Cys Gln Leu Leu
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Peptide

<400> SEQUENCE: 124

Ala Val Ile Pro Ile Asn Gly Ser Pro Arg Thr Pro Arg
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Peptide

<400> SEQUENCE: 125

Asp Glu Ile Cys Ile Ala Gly Ser Pro Leu Thr Pro Arg
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Peptide

<400> SEQUENCE: 126

Gly Leu Gly Arg Ser Ile Thr Ser Pro Thr Thr Leu Tyr
1               5                   10

<210> SEQ ID NO 127
<211> LENGTH: 13
<212> TYPE: PRT
<213> ORGANISM: Artificial Sequence
<220> FEATURE:
<223> OTHER INFORMATION: Peptide

<400> SEQUENCE: 127

Asp Arg Thr Ser Arg Asp Ser Ser Pro Val Met Arg Ser
1               5                   10

<210> SEQ ID NO 128
<211> LENGTH: 13
<212> TYPE: PRT
<213> ORGANISM: Artificial Sequence
<220> FEATURE:
```

```
<223> OTHER INFORMATION: Peptide

<400> SEQUENCE: 128

Lys Met Gln Leu Arg Arg Pro Ser Asp Gln Glu Val Ser
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Peptide

<400> SEQUENCE: 129

Ile Ala Lys Arg Arg Arg Leu Ser Ser Leu Arg Ala Ser
1               5                   10

<210> SEQ ID NO 130
<211> LENGTH: 13
<212> TYPE: PRT
<213> ORGANISM: Artificial Sequence
<220> FEATURE:
<223> OTHER INFORMATION: Peptide

<400> SEQUENCE: 130

Val Arg Arg Leu Arg Arg Leu Thr Ala Arg Glu Ala Ala
1               5                   10

<210> SEQ ID NO 131
<211> LENGTH: 13
<212> TYPE: PRT
<213> ORGANISM: Artificial Sequence
<220> FEATURE:
<223> OTHER INFORMATION: Peptide

<400> SEQUENCE: 131

Lys Asn Gly Cys Arg Arg Gly Ser Ser Leu Gly Gln Ile
1               5                   10

<210> SEQ ID NO 132
<211> LENGTH: 13
<212> TYPE: PRT
<213> ORGANISM: Artificial Sequence
<220> FEATURE:
<223> OTHER INFORMATION: Peptide

<400> SEQUENCE: 132

Leu Ile Glu Asp Asn Glu Tyr Thr Ala Arg Gln Gly Ala
1               5                   10

<210> SEQ ID NO 133
<211> LENGTH: 13
<212> TYPE: PRT
<213> ORGANISM: Artificial Sequence
<220> FEATURE:
<223> OTHER INFORMATION: Peptide

<400> SEQUENCE: 133

Lys Thr Pro Ser Ser Pro Val Tyr Gln Asp Ala Val Ser
1               5                   10

<210> SEQ ID NO 134
<211> LENGTH: 13
<212> TYPE: PRT
<213> ORGANISM: Artificial Sequence
<220> FEATURE:
<223> OTHER INFORMATION: Peptide
```

```
<400> SEQUENCE: 134

Ser Ser Arg Arg Thr Thr Leu Cys Gly Thr Leu Asp Tyr
1               5                   10

<210> SEQ ID NO 135
<211> LENGTH: 13
<212> TYPE: PRT
<213> ORGANISM: Artificial Sequence
<220> FEATURE:
<223> OTHER INFORMATION: Peptide

<400> SEQUENCE: 135

Ala Ala Gly Glu Arg Arg Lys Ser Gln Glu Ala Gln Val
1               5                   10

<210> SEQ ID NO 136
<211> LENGTH: 13
<212> TYPE: PRT
<213> ORGANISM: Artificial Sequence
<220> FEATURE:
<223> OTHER INFORMATION: Peptide

<400> SEQUENCE: 136

Gly Ser Arg Ser Arg Thr Pro Ser Leu Pro Thr Pro Pro
1               5                   10

<210> SEQ ID NO 137
<211> LENGTH: 13
<212> TYPE: PRT
<213> ORGANISM: Artificial Sequence
<220> FEATURE:
<223> OTHER INFORMATION: Peptide

<400> SEQUENCE: 137

Glu Pro Pro Ser Pro Ala Thr Thr Pro Cys Gly Lys Val
1               5                   10

<210> SEQ ID NO 138
<211> LENGTH: 13
<212> TYPE: PRT
<213> ORGANISM: Artificial Sequence
<220> FEATURE:
<223> OTHER INFORMATION: Peptide

<400> SEQUENCE: 138

Glu His Ile Glu Arg Arg Val Ser Asn Ala Gly Gly Pro
1               5                   10

<210> SEQ ID NO 139
<211> LENGTH: 13
<212> TYPE: PRT
<213> ORGANISM: Artificial Sequence
<220> FEATURE:
<223> OTHER INFORMATION: Peptide

<400> SEQUENCE: 139

Gly Ala Lys Leu Arg Lys Val Ser Lys Gln Glu Glu Ala
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Peptide
```

```
<400> SEQUENCE: 140

Leu Ala Arg Arg Arg Lys Ala Thr Gln Val Gly Glu Lys
1               5                   10

<210> SEQ ID NO 141
<211> LENGTH: 13
<212> TYPE: PRT
<213> ORGANISM: Artificial Sequence
<220> FEATURE:
<223> OTHER INFORMATION: Peptide

<400> SEQUENCE: 141

Glu Glu Lys Lys Lys Lys Thr Thr Thr Ile Ala Val Glu
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Peptide

<400> SEQUENCE: 142

Asn Gln Asn Ser Arg Arg Pro Ser Arg Ala Thr Trp Leu
1               5                   10
```